(12) United States Patent
Feinberg et al.

(10) Patent No.: US 9,322,015 B2
(45) Date of Patent: Apr. 26, 2016

(54) METHODS OF USING MICRORNA-26A TO PROMOTE ANGIOGENESIS

(75) Inventors: Mark W. Feinberg, Newton, MA (US); Basak Icli, Wellesley, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 0 days.

(21) Appl. No.: 14/003,886

(22) PCT Filed: Mar. 9, 2012

(86) PCT No.: PCT/US2012/028417
§ 371 (c)(1),
(2), (4) Date: Dec. 23, 2013

(87) PCT Pub. No.: WO2012/122447
PCT Pub. Date: Sep. 13, 2012

(65) Prior Publication Data
US 2014/0121262 A1 May 1, 2014

Related U.S. Application Data
(60) Provisional application No. 61/450,752, filed on Mar. 9, 2011.

(51) Int. Cl.
| | | |
|---|---|---|
| A61K 48/00 | (2006.01) | |
| C07H 21/02 | (2006.01) | |
| C07H 21/04 | (2006.01) | |
| C12N 15/113 | (2010.01) | |
| C12Q 1/68 | (2006.01) | |

(52) U.S. Cl.
CPC ............ *C12N 15/113* (2013.01); *C12Q 1/6883* (2013.01); *C12Q 1/6886* (2013.01); *C12N 2310/141* (2013.01); *C12Q 2600/158* (2013.01); *C12Q 2600/178* (2013.01)

(58) Field of Classification Search
CPC .............................. C12N 15/113; A61K 48/00
See application file for complete search history.

(56) References Cited

U.S. PATENT DOCUMENTS

2009/0298916 A1  12/2009  Kauppinen et al.

FOREIGN PATENT DOCUMENTS

| EP | 2228444 | 9/2010 |
|---|---|---|
| WO | 2011/084460 | 7/2011 |
| WO | 2012/065024 | 5/2012 |

OTHER PUBLICATIONS

Icli, "MicroRNA-Mediated Regulation of SMAD1 in the Vascular Endothelium Promotes Cell Growth Arrest," Journal of the American College of Cardiology, 57(14):E2045 (2011).

Leeper et al., "MicroRNA-26a is a novel regulator of vascular smooth muscle cell function," Journal of Cellular Physiology, 226(4):1035-1043 (2011).
Supplementary European Search Report issued in EP12755531 on Sep. 26, 2014 (6 pages).
Asangani et al., "MicroRNA-21 (miR-21) post-transcriptionally downregulates tumor suppressor Pdcd4 and stimulates invasion, intravasation and metastasis in colorectal cancer," Oncogene, 27(15):2128-36 (2008).
Bolli et al., "Myocardial protection at a crossroads: the need for translation into clinical Therapy," Circ. Res., 95(2):125-34 (2004).
Bonauer et al., "MicroRNA-92a controls angiogenesis and functional recovery of ischemic tissues in mice," Science, 324(5935):1710-3 (2009).
Bonauer et al., "Vascular microRNAs," Curr. Drug Targets, 11(8):943-949 (2010).
Carmeliet, P., "Mechanisms of angiogenesis and arteriogenesis," Nat. Med, 6(4):389-95 (2000).
Ciarrocchi et al., "Id1 restrains p21 expression to control endothelial progenitor cell formation," PLoS One, 2(12):e1338 (2007).
Cross et al., "FGF and VEGF function in angiogenesis: signalling pathways, biological responses and therapeutic inhibition," Trends Pharmacol Sci, 22(4):201-7 (2001).
Dews et al., "Augmentation of tumor angiogenesis by a Myc-activated microRNA cluster," Nat. Genet., 38(9):1060-5 (2006).
Esquela-Kerscher et al., "Oncomirs—microRNAs with a role in cancer," Nat. Rev. Cancer, 6(4):259-69 (2006).
Fadini et al., "Critical Reevaluation of Endothelial Progenitor Cell Phenotypes for Therapeutic and Diagnostic Use," Circ. Res., 110:624-637 (2012).
Fasanaro et al., "MicroRNA-210 modulates endothelial cell response to hypoxia and inhibits the receptor tyrosine kinase ligand Ephrin-A3," J. Biol. Chern., 283(23):15878-83 (2008).
Ferrara, N., "Role of vascular endothelial growth factor in the regulation of angiogenesis," Kidney Int, 56(3):794-814 (1999).
Folkman et al., "Angiogenesis," J. Biol Chern, 267(16):10931-4 (1992).
He et al., "A microRNA polycistron as a potential human oncogene," Nature, 435(7043):828-33 (2005).
International Preliminary Report on Patentability issued in PCT/US2012/028417 on Sep. 10, 2013(7 pages).
Kota et al., "Therapeutic microRNA delivery suppresses tumorigenesis in a murine liver cancer model," Cell, 137(6):1005-17 (2009).
Langenfeld et al., "Bone morphogenetic protein 2 stimulation of tumor growth involves the activation of Smad-1/5," Oncogene, 25(5):685-92 (2006).
Lewis et al., "Conserved See Pairing, Often Flanked by Adenosines, Indicates that Thousands of Human Genes are MicroRNA Targets," Cell, 120(1):15-20 (2005).
Luzi, E., et al., "Osteogenic Differentiation of Human Adipose Tissue-Derived Stem Cells is Modulated by the miR-26a Targeting of the SMAD1 Transcription Factor," J. Bone Miner. Res., 23(2):287-95 (2008).
Maglione et al., "Isolation of a human placenta cDNA coding for a protein related to the vascular permeability factor," Proc. Natl. Acad. Sci. USA, 88(20):9267-71 (1991).

(Continued)

*Primary Examiner* — Amy Bowman
(74) *Attorney, Agent, or Firm* — Fish & Richardson P.C.

(57) ABSTRACT

Methods for promoting angiogenesis, and for diagnosing the presence or risk of developing disorders associated with impaired angiogenesis or blood flow to a tissue in the body, using microRNA-26a (miR-26a).

8 Claims, 24 Drawing Sheets

(56) References Cited

OTHER PUBLICATIONS

Maglione et al., "Two alternative mRNAs coding for the angiogenic factor, placenta growth factor (PlGF), are transcribed from a single gene of chromosome 14," Oncogene, 8(4):925-31 (1993).
Melero-Martin et al., "Chapter 13. An in vivo experimental model for postnatal vasculogenesis," Methods Enzymol., 445:303-29 (2008).
Ota et al., "Identification and characterization of a novel gene, C13orf25, as a target for 13q31-q32 amplification in malignant lymphoma," Cancer Res., 64(9):3087-95 (2004).
Poliseno et al., "MicroRNAs modulate the angiogenic properties of HUVECs," Blood, 108(9):3068-71 (2006).
Pulkkinen et al., "Hypoxia induces microRNA miR-210 in vitro and in vivo ephrin-A3 and neuronal pentraxin 1 are potentially regulated by miR-210," FEBS Lett., 582(16):2397-401 (2008).
Risau, W., "Mechanisms of angiogenesis," Nature, 386(6626):671-4 (1997).
Shing et al., "Heparin affinity: purification of a tumor-derived capillary endothelial cell growth factor," Science, 223(4642):1296-9 (1984).
Tsai et al., "The M type K15 protein of Kaposi's sarcoma-associated herpesvirus regulates microRNA expression via its SH2-binding motif to induce cell migration and invasion," J. Virol., 83(2):622-32 (2009).
Urbich et al., "Role of microRNAs in vascular diseases, inflammation, and angiogenesis," Cardiovasc. Res., 79(4):581-8 (2008).
van Rooij et al., "Toward microRNA-based therapeutics for heart disease: the sense in antisense," Circ. Res., 103(9):919-28 (2008).
Venturini et al., "Expression of the miR-17-92 polycistron in chronic myeloid leukemia (CML) CD34+ cells," Blood, 109(10):4399-405 (2007).
Wang et al., "AngiomiRs—key regulators of angiogenesis," Curr. Opin. Genet. Dev., 19(3):205-11 (2009).
Wenger et al., "miR-296 regulates growth factor receptor overexpression in angiogenic endothelial cells," Cancer Cell, 14(5):382-93(2008).
Yu et al., "Bone morphogenetic protein (BMP) type II receptor is required for BMP-mediated growth arrest and differentiation in pulmonary artery smooth muscle cells," J. Biol. Chem., 283(7):3877-88 (2008).
International Search Report and Written Opinion mailed Jul. 12, 2012 in international application No. PCT/US2012/028417, 8 pages.
Luzi et al., Osteogenic differentiation of human adipose tissue-derived stem cells is modulated by the miR26a targeting of the SMAD1 transcription factor. J Bone Miner Res. 23(2):287-95, abstract only (2008).
Masaki et al., "Smad1 Protects Cardiomyocytes From Ischemia-Reperfusion Injury," Circulation 111:2752-2759 (2005).
Database GenBank, Ac No. AJ421747.1 (Nov. 6, 2003).
Mohamed et al., "Mechanical Stretch Up-regulates MicroRNA-26a and Induces Human Airway Smooth Muscle Hypertrophy by Suppressing Glycogen Synthase Kinase-3b," The Journal of Biological Chemistry 285(38): 29336-29347 (2010).
Tao Yu et al., "The expression profile of microRNAs in a model of 7, I2-dimethyl-benz [a]anthrance-induced oral carcinogenesis in Syrian hamster," Journal of Experimental & Clinical Cancer Research 28:64-73 (2009). Retrieved from the Internet: URL: <http://www.jeccr.com/content/28/1/64> pp. 1-10.

```
       g        U          C                    --g  ca
gug  ccucgU  CAAGUAAUC  AGGAUAGGCU       ug     g
|||  ||||||  |||||||||  ||||||||||       ||     g
cgc  gggGCA  GUUCAUUGG  UCUUAUCCgg       ac     u
       a        C          U                    gua  cc
```

FIG. 5A

```
        gg  ug   UU             C                       guuucc
ggcugu   c   ga     CAAGUAAUC  AGGAUAGGCU               a
||||||   |   ||     |||||||||  ||||||||||
ucgacg   g   CU     GUUCAUUAG  UCUUAUCCgg               u
        ga  gu   UU             U                       aguguc
```

FIG. 5B

```
       ga   -    U              UC              u   ug
ccgg    ccc  agU  CAAGUAAU   AGGAUAGGUug  g      c
||||    |||  |||  ||||||||   ||||||||||   |
ggcc    ggg  UCG  GUUCAUUA   UCUUGUCCgac  c      u
       ag    C    -             CC              -   ug
```

METHODS OF USING MICRORNA-26A TO PROMOTE ANGIOGENESIS

CLAIM OF PRIORITY

This application is a U.S. National Phase Application under 35 U.S.C. §371 of International Patent Application No. PCT/US2012/028417, filed on Mar. 9, 2012, which claims the benefit of U.S. Provisional Patent Application Ser. No. 61/450,752, filed on Mar. 9, 2011. The entire contents of the foregoing are hereby incorporated by reference.

FEDERALLY SPONSORED RESEARCH OR DEVELOPMENT

This invention was made with Government support under Grant No. R01HL091076 awarded by the National Institutes of Health. The Government has certain rights in the invention.

TECHNICAL FIELD

This invention relates to methods for promoting angiogenesis, and for diagnosing the presence or risk of developing disorders associated with impaired angiogenesis or blood flow to a tissue in the body, using microRNA-26a (miR-26a).

BACKGROUND

Neoangiogenesis is critical for tissue repair in response to injury such as myocardial infarction (MI) or peripheral artery disease. It has been shown that growth factors such as vascular endothelial cell growth factor (VEGF), tumor necrosis factor-alpha (TNF-a), basic fibroblast growth factor (bFGF), or placenta growth factor (PlGF) are potent regulators of angiogenesis. Binding of these angiogenic factors to their receptors may activate a cascade of signaling events including the activation of phosphinositide 3-kinase (PI3K) and mitogen activated protein kinase (MAPK). In response to pro-angiogenic stimuli, vascular endothelial cells (ECs) are activated to migrate to distant sites and proliferate to form new primary capillaries from the pre-existing vascular network (Carmeliet, P., Nat Med, 2000. 6(4): p. 389-95; Cross, M. J. and L. Claesson-Welsh, Trends Pharmacol Sci, 2001. 22(4): p. 201-7; Ferrara, N., Kidney Int, 1999. 56(3): p. 794-814; Folkman, J. and Y. Shing, J Biol Chem, 1992. 267(16): p. 10931-4; Maglione, D., et al., Proc Natl Acad Sci USA, 1991. 88(20): p. 9267-71; Maglione, D., et al., Oncogene, 1993. 8(4): p. 925-31; Risau, W., Nature, 1997. 386(6626): p. 671-4; and Shing, Y., et al., Science, 1984. 223(4642): p. 1296-9). However, despite the importance of ECs in neoangiogenesis, the mechanisms regulating this process remain poorly understood.

SUMMARY

At least in part, the present invention is based on the discovery that miR-26a is a critical regulator of EC growth and angiogenesis. As shown herein by gain and loss-of-function approaches, miR-26a specifically targets Smad1 signaling in ECs, thereby reducing the downstream target gene ID1, a basic-helix-loop-helix protein known to inhibit cell cycle inhibitors p21 WAF/CIP and p27, and inducing cell cycle arrest. Furthermore, targeting miR-26a using a specific LNA-antagomir induces robust angiogenesis in vivo using a mouse model of acute myocardial infarction (MI). These data provide the foundation for a therapeutic strategy to promote angiogenesis under pathological disease states such as acute MI.

In a first aspect, the invention provides the use of an inhibitory nucleic acid targeting microRNA-26a (miR-26a) and/or miR-26b in the treatment of a disorder associated with impaired angiogenesis or blood flow to a tissue in the body in a subject.

In another aspect, the invention provides methods for treating a disorder associated with impaired angiogenesis or blood flow to a tissue in the body in a subject. The methods include administering to the subject a therapeutically effective amount of an inhibitory nucleic acid targeting microRNA-26a (miR-26a) and/or miR-26b.

In some embodiments, the inhibitory nucleic acid comprises the sequence ACTTGA (SEQ ID NO:5).

In some embodiments, the inhibitory nucleic acid is an antagomir.

In some embodiments, the inhibitory nucleic acid comprises one or more locked nucleotides.

In some embodiments, the disorder is selected from the group consisting of ischemic heart disease, coronary artery disease, ischemic heart failure, peripheral artery disease (PAD), critical limb ischemia, and diabetic foot ulcers.

In another aspect, the invention provides methods for diagnosing a disorder associated with impaired angiogenesis or blood flow to a tissue in the body in a subject. The methods include determining a level of miR-26a and/or miR-26b in a sample from the subject; and comparing the level of miR-26a and/or miR-26b in the sample to a corresponding reference level (i.e., of miR-26a and/or miR-26b). The presence of a level of miR-26a and/or miR-26b in the subject that is above the reference level indicates that the subject has a disorder associated with impaired angiogenesis or blood flow to a tissue in the body.

In another aspect, the invention provides methods for determining risk of developing a disorder associated with impaired angiogenesis or blood flow to a tissue in the body. The methods include determining a level of miR-26a and/or miR-26b in a sample from the subject; and comparing the level of miR-26a and/or miR-26b in the sample to a reference level of miR-26a. The presence of a level of miR-26a and/or miR-26b in the subject that is above the reference level indicates that the subject is at risk of developing a disorder associated with impaired angiogenesis or blood flow to a tissue in the body.

In some embodiments, the disorder is selected from the group consisting of ischemic heart disease, coronary artery disease, ischemic heart failure, peripheral artery disease (PAD), critical limb ischemia, and diabetic foot ulcers.

In some embodiments, determining a level of miR-26a in the subject comprises detecting a level of a nucleic acid comprising the sequence UUCAAGUAAUCCAGGAUAGGCU (SEQ ID NO:3), and/or a nucleic acid comprising the sequence CCUAUUCUUGGUUACUUGCACG-70 (SEQ ID NO:9). In some embodiments, determining a level of miR-26b in the subject comprises detecting a level of a nucleic acid comprising the sequence UUCAAGUAAUU-CAGGAUAGGU (SEQ ID NO:11), and/or a nucleic acid comprising the sequence CCUGUUCUCCAUUACUUG-GCUC (SEQ ID NO:12).

In some embodiments, the sample comprises serum from the subject.

In some embodiments, the subject is a mammal, e.g., a human.

As used herein, a "disorder associated with impaired angiogenesis or blood flow to a tissue in the body" is a disorder that is associated with ischemia or reduced angiogenesis or vascularization typically producing inadequate blood flow to a part of the body, wherein a subject with the disorder would benefit from increased angiogenesis.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 5A-5C. Schematic illustrations of the stem-loop structures of human mir-26a-1 (5A; SEQ ID NO:1), mir-26a-2 (5B; SEQ ID NO:2) and mir-26b (5C; SEQ ID NO:10).

DETAILED DESCRIPTION

MicroRNAs (miRs) are small 20-22 nucleotide, non-coding RNAs capable of repressing gene expression by base pairing at the 3' untranslated regions (3'-UTRs) of mRNA targets. It has been predicted that miRs target thousands of genes and regulate a third of protein encoding genes (Lewis, B. P., C. B. Burge, and D. P. Bartel, Cell, 2005. 120(1): p. 15-20). MiRs play diverse roles in physiological and pathological disease states from regulating cardiovascular development and hematopoietic lineage differentiation to cancer and heart disease (Esquela-Kerscher, A. and F. J. Slack, Nat Rev Cancer, 2006. 6(4): p. 259-69; Urbich, C., A. Kuehbacher, and S. Dimmeler, Cardiovasc Res, 2008. 79(4): p. 581-8; van Rooij, E., W. S. Marshall, and E. N. Olson, Circ Res, 2008. 103(9): p. 919-28). For example, the miR-17~92 cluster also known as OncomiR-1 was shown to be upregulated in tumors (He, L., et al., Nature, 2005. 435(7043): p. 828-33; Ota, A., et al., Cancer Res, 2004. 64(9): p. 3087-95; Venturini, L., et al., Blood, 2007. 109(10): p. 4399-405) and overexpression of it promoted tumor angiogenesis (Dews, M., et al., Nat Genet, 2006. 38(9): p. 1060-5). Recently, one member of this miR-17~92 cluster, miR-92a, was shown to be highly expressed in ECs and overexpression of miR-92a blocked angiogenesis both in-vitro and in-vivo (Bonauer, A., et al., Science, 2009. 324(5935): p. 1710-3).

Figure 4:
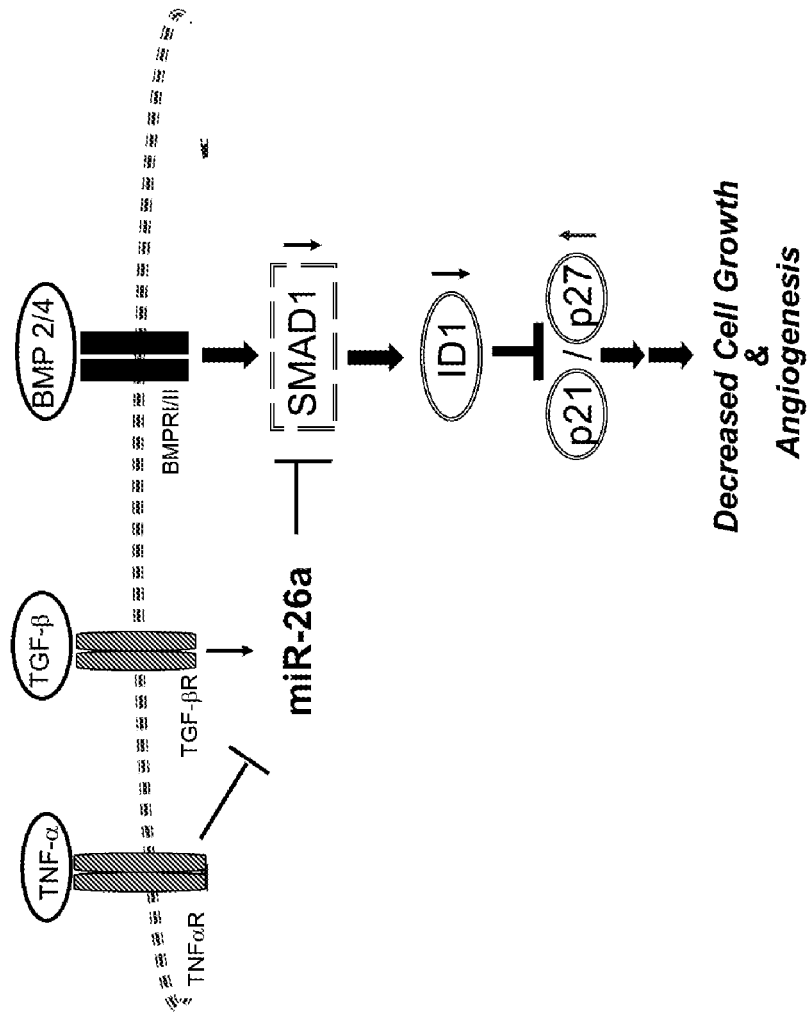
FIG. 4. Exemplary illustration of a proposed mechanism by which miR-26a exerts anti-angiogenic properties in vitro and in vivo. Without wishing to be bound by theory, miR-26a may be regulated by pro and anti-angiogenic factors. Induction of miR-26a is believed to decrease cell growth and angiogenesis via targeting the SMAD1-Id-1-p21$^{WAF/CIP1}$-p27 signaling pathway.

Accumulating studies suggest an important role of several microRNAs in angiogenesis, particularly in the context of tumor biology (Wang, S. and E. N. Olson, Curr Opin Genet Dev, 2009. 19(3): p. 205-11; Bonauer, A., R. A. Boon, and S. Dimmeler, Curr Drug Targets. 11(8): p. 943-9). However, the identification of the critical miRs in the context of vascular EC growth and MI is not well understood. As described herein, miR-26a is an anti-angiogenic miR in ECs, first identified by a microarray profiling approach. As demonstrated using gain and loss-of-function approaches, miR-26a specifically targets Smad1 signaling in ECs, an effect that decreases the downstream target gene Id1, a basic-helix-loop-helix protein known to inhibit cell cycle inhibitors p21$^{WAF/CIP1}$ and p27, and induces endothelial cell cycle arrest. Conversely, in response to pro-angiogenic stimuli such as TNF-α, miR-26a expression is reduced, an effect that allows for increased Smad1 and Id1 expression and reduced expression of cell cycle regulators p21$^{WAF/CIP1}$ and p27 (see hypothetical schema in FIG. 4). MiR-26a overexpression had profound inhibitory effects on endothelial cell growth, cell cycle progression, migration, and the release of the pro-angiogenic growth factor VEGF. Furthermore, targeting miR-26a using a specific LNA-antagomiR induces robust angiogenesis in vivo using a mouse model of acute myocardial infarction (MI). These data provide the foundation for a novel therapeutic strategy to promote angiogenesis under pathological disease states such as acute MI.

In addition to miR-26a, other miRs have been recently identified to be important in regulating angiogenesis in vivo. In particular, miR-92a, part of the OncomiR-1 cluster, was found to inhibit endothelial cell growth in vitro and in vivo. Interestingly, inhibition of miR-92a also reduced infarct size and promoted neovascularization after 1 week using an analogous LAD-ligation MI model. However, the targets identified for miR-92a were quite different than miR-26a's targets and included integrin-alpha5 and eNOS. Other miRs implicated in angiogenesis that have been reported including miR-221, miR-222, and miR-126 were also identified as differentially regulated in our microarray studies. Several other microRNAs that have been implicated in angiogenesis include miR-210, which has been identified as a hypoxia-inducible miR (Fasanaro, P., et al., J Biol Chem, 2008. 283(23): p. 15878-83; Pulkkinen, K., et al., FEBS Lett, 2008. 582(16): p. 2397-401), miR-296 (Wurdinger, T., et al., Cancer Cell, 2008. 14(5): p. 382-93), miR-21, and miR-31 (Tsai, Y. H., et al., J Virol, 2009. 83(2): p. 622-32; Asangani, I. A., et al., Oncogene, 2008. 27(15): p. 2128-36), which are postulated to be pro-angiomiRs, particularly in the context of tumor-associated angiogenesis. Finally, miR-221 and miR-222 are examples of miRs that can impair angiogenesis in ECs, smooth muscle cells (SMC) and hematopoietic progenitor cells (HPC) in vitro, in part, by targeting c-Kit (Poliseno, L., et al., Blood, 2006. 108(9): p. 3068-71).

Using bioinformatics approaches, potential genes regulated by miR-26a were identified. A BMP signaling effector and upstream modulator of Id1 (Yu, P. B., et al., J Biol Chem, 2008. 283(7): p. 3877-88), SMAD1, was a common gene predicted highly by multiple bioinformatics database programs. Given the effect of miR-26a on cell growth and migration, SMAD1 was selected as a potential signaling molecule of miR-26a's actions. Consistent with these findings, miR-26a has been shown to target SMAD1 in osteoblasts (Luzi, E., et al., J Bone Miner Res, 2008. 23(2): p. 287-95). Kota et al. has previously reported that miR-26a expression in liver cancer cells induces cell cycle arrest through direct targeting of cyclins D2 and E2 (Kota, J., et al., Cell, 2009. 137(6): p. 1005-17). Although their cell cycle growth arrest findings are consistent with the present study, the mechanism in hepatoma cells appear to be quite different than the results reported herein. The present studies showed that miR-26a causes cell cycle and growth arrest in HUVECs through direct targeting the Id1-p21$^{WAF/CIP1}$-p27 pathway. In addition, no effect of miR-26a was observed on cyclin D2 or cyclin E2 in HUVECs. This could be attributed to the fact that the present experiments used a more physiologically relevant primary cell line, whereas Kote et al. used transformed cell lines.

Thus, the signaling pathways and targets regulating the biology of these two model systems are likely to be quite different.

Id1, a known Smad1 target gene, has been implicated in tumor-associated angiogenesis. Indeed, Id1 knockout mice exhibited reduced angiogenesis and increased p21$^{WAF/CIP1}$ expression in several cell types. Furthermore, genetic ablation of p21$^{WAF/CIP1}$ in Id1 knockout mice restored a functional endothelial cell population and rescued the defective angiogenesis and tumor growth (Ciarrocchi, A., et al., PLoS One, 2007. 2(12): p. e1338). Inhibition of Id1 after metastasis also inhibited angiogenesis and increased the survival of tumor-bearing mice. Interestingly, administration of recombinant BMP-2, an upstream growth factor that activates Smad1, also stimulated angiogenesis in developing lung tumors (Langenfeld, E. M., Y. Kong, and J. Langenfeld, Oncogene, 2006. 25(5): p. 685-92). Thus, the present findings that miR-26a can regulate the downstream Smad1-Id1-p21$^{WAF/CIP1}$-p27 signaling pathway in endothelial cells is consistent with observed effects in response to perturbation of this signaling pathway in the context of tumor-associated angiogenesis and may provide therapeutic opportunities for regulating tumor growth.

Methods of Treatment

The methods described herein include methods for the treatment of disorders associated with impaired angiogenesis or blood flow to a tissue in the body, e.g., ischemic heart disease, coronary artery disease, ischemic heart failure, peripheral artery disease (PAD), critical limb ischemia, and diabetic foot ulcers. In some embodiments, the disorder is associated with an ischemic insult and would benefit from increased angiogenesis, e.g., to reduce infarct size. Generally, these methods include administering a therapeutically effective amount of an inhibitory nucleic acid targeting miR-26a as described herein, to a subject who is in need of, or who has been determined to be in need of, such treatment. The inhibitory nucleic acid can be administered parenterally, topically, orally or by local administration, such as by aerosol or transdermally, though parenteral administration will be most typical. In some embodiments, the inhibitory nucleic acid will be administered intravenously, e.g., into the vasculature of the organ or tissue affected by the disorder or ischemic insult. Thus, for a subject having PAD, the inhibitory nucleic acid can be administered into the peripheral vasculature. For a subject having diabetic foot ulcers, the inhibitory nucleic acid can be administered into the vasculature of the affected foot. For diseases associated with reduced angiogenesis or ischemia of cardiac tissues, the inhibitory nucleic acid can be administered using intracoronary administration.

As used in this context, to "treat" means to ameliorate at least one symptom of the disorder associated with impaired angiogenesis or blood flow to a tissue in the body. Often, an ischemic insult results in tissue necrosis or infarction; thus, administration of a therapeutically effective amount of an inhibitory nucleic acid targeting miR-26a as described herein can result in increased vascularization, a reduction in necrosis and infarct size, and a return or approach to normal organ function.

Acute coronary syndrome (ACS) refers to symptoms compatible with acute myocardial ischemia and includes unstable angina (UA), non-ST-segment elevation myocardial infarction (NSTEMI), and ST-segment elevation myocardial infarction (STEMI), all of which are typically associated with coronary atherosclerosis. Methods are known in the art for diagnosing ACS, see, e.g., Kumar and Cannon, Mayo Clin Proc. 2009 October; 84(10):917-38; and Kalra et al., Postgrad Med. 2008 April; 120(1):18-27.

Ischemic heart disease (IHD) is the one of the leading causes of morbidity and mortality worldwide (Cannon, R. O., 3rd, Nat Clin Pract Cardiovasc Med, 2005. 2(2): p. 88-94). IHD is induced by an insufficient blood supply of the heart muscle and hypoxia-related loss of the viable heart tissue. This event is usually a consequence of coronary artery disease or myocardial infarction (MI) (Bolli, R., et al., Circ Res, 2004. 95(2): p. 125-34). In response to cardiac injury, neoangiogenesis ensues where pro-angiogenic growth factors are secreted that promote endothelial cell proliferation and migration within damaged tissues as part of the reparative process.

Coronary artery disease (CAD) is the result of accumulation of atheromatous plaques within the coronary arteries that supply the myocardium. Peripheral Artery Disease (which as used herein includes peripheral vascular disease or PVD) is characterized by the presence of impaired circulation to the limbs, typically as a result of the presence of atherosclerotic plaques. Subjects with PAD have a very high risk of fatal and non-fatal cerebrovascular and cardiovascular events.

Chronic critical limb ischemia (CLI) is a severe form of PAD in which a severe blockage in the arteries of the lower extremities markedly reduces blood-flow. CLI is diagnosed in the presence of more than two weeks of pain when at rest, non-healing ulcers, or tissue loss. CLI is associated with great mortality and morbidity, including limb loss.

Diabetic foot ulcers can arise as a result of a number of factors, including atherosclerotic peripheral vascular disease, peripheral neuropathy, and alterations in the bony structures of the foot.

Methods for diagnosing these conditions (i.e., for identifying subjects in need of treatment with a method described herein) are known in the art. Risk factors for these conditions include: age; smoking; diabetes; overweight or obesity; sedentary lifestyle; high cholesterol; high blood pressure; and family history of atherosclerosis or claudication.

Inhibitory Nucleic Acids

In some embodiments, the methods described herein include the administration of a therapeutically effective amount of an inhibitory nucleic acid that targets miR-26a. In general, a sequence of miR-26a from the same species as the subject to be treated is used as the target sequence. For example, when treating human subjects, human miR-26a is used. In the methods described herein, any of the following can be used as target sequences.

The sequence of the human miR-26a-1 stem-loop (Chromosome 3; see FIG. 5A) is as follows:

```
                                        (SEQ ID NO: 1)
  1-GUGGCCUCGUUCAAGUAAUCCAGGAUAGGCUGUGCAGGUCC

CAAUGGGCCUAUUCUUGGUUACUUGCACGGGGACGC-71
```

The sequence of the human miR-26a-2 stem-loop (Chromosome 12; see FIG. 5B) is as follows:

```
                                        (SEQ ID NO: 2)
  1-GGCUGUGGCUGGAUUCAAGUAAUCCAGGAUAGGCUGUUUC

CAUCUGUGAGGCCUAUUCUUGAUUACUUGUUUCUGGAGGCAG

CU-84
```

The mature sequence of human miR-26a (also known as hsa-miR-26a-5p) is as follows (numbering relative to mature miR-26a-1 stem-loop):

10-UUCAAGUAAUCCAGGAUAGGCU-31 (SEQ ID NO: 3)

The seed sequence of human miR-26a is as follows:

1-UCAAGU-6 (SEQ ID NO: 4)

The mature sequence of human mir-26a-1* (also known as hsa-miR-26a-1-3-p) is as follows:

49-CCUAUUCUUGGUUACUUGCACG-70 (SEQ ID NO: 9)

The sequences of the mature miR-26a (also known as hsa-miR-26a-5p) and miR-26-a1* (also known as hsa-miR-26a-1-3-p) are shown in bold on FIGS. 5A-5B.

Sequences for miR-26a from other species are known in the art.

Although miR-26a has been referred to herein, in some embodiments, the methods described herein include targeting miR-26b as an alternative to or in addition to miR-26a.

The sequence of the human miR-26b stem loop (Chromosome 2; see FIG. 5C) is as follows:

1-CCGGGACCCAGUUCAAGUAAUUCAGGAUAGGUUGUG
UGCUGUCCAGCCUGUUCUCCAUUACUUGGCUCGGGGAC
CGG-77 (SEQ ID NO: 10)

The mature sequence of human miR-26b (also known as hsa-miR-26b-5p) is as follows (numbering relative to mature miR-26a-1 stem-loop):

12-UUCAAGUAAUUCAGGAUAGGU-32 (SEQ ID NO: 11)

The seed sequence of human miR-26b is as follows:

1-UCAAGU-6 (SEQ ID NO: 4)

The mature sequence of human mir-26b-1* (also known as hsa-miR-26b-3-p) is as follows:

47-CCUGUUCUCCAUUACUUGGCUC-68 (SEQ ID NO: 12)

The sequences of the mature miR-26a (also known as hsa-miR-26a-5p) and miR-26-a1* (also known as hsa-miR-26a-1-3-p) are shown in bold on FIG. 5C.

In some embodiments, the inhibitory nucleic acid is a competitive antagomiR that blocks the ability of miR-26a to bind to the 3'-UTR of target genes, e.g., SMAD1.

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), antagomirs, peptide nucleic acids (PNAs), and other oligomeric compounds or oligonucleotide mimetics which hybridize to at least a portion of the target nucleic acid (i.e., miR-26a, e.g., all or part of any of SEQ ID NOs:1-4 or 9, or miR-26b, e.g., all or part of SEQ ID NOs: 10-12) and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010/040112.

In some embodiments, the inhibitory nucleic acids are 5, 6, 7, 8, 9, or 10, e.g., 10 to 50, 13 to 50, or 13 to 30 or more, nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies inhibitory nucleic acids having antisense portions of 12, 13, 14, 15, 16, 17, 18, 19, 20, 21, 22, 23, 24, 25, 26, 27, 28, 29 or 30 nucleotides in length, or any range therewithin.

In some embodiments, the inhibitory nucleic acids are designed to target a specific region of miR-26a. For example, a specific functional region can be targeted, e.g., a region comprising a seed sequence or a region complementary to the target nucleic acid on which the miR-26a acts. For example, the inhibitory nucleic acid can be designed to target nucleotides 2-7 of the mature miR-26a, e.g., complementary to UCAAGU (SEQ ID NO:4), e.g., comprise or have the sequence ACTTGA (SEQ ID NO:5). In some embodiments, the inhibitory nucleic acid comprises or has the sequence ATTACTTGA (SEQ ID NO:6); TTACTTGA (SEQ ID NO:7); or TACTTGA (SEQ ID NO:8). See, e.g. US 2009/0298916.

Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

In some embodiments, the inhibitory nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, ~N($CH_3$)~O~$CH_2$ (known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—CH); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, $SCH_3$, F, OCN, $OCH_3OCH_3$, $OCH_3O(CH_2)nCH_3$, $O(CH_2)nNH_2$ or $O(CH_2)nCH_3$ where n is from 1 to about 10; Ci to C10 lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy (2'-0-$CH_2CH_2OCH_3$, also known as 2'-O-(2-methoxyethyl)) (Martin et al, Helv. Chim. Acta, 1995, 78, 486). Other preferred modifications include 2'-methoxy (2'-0-$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539, 082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. No. 4,845,205; U.S. Pat. No. 5,130,302; U.S. Pat. No. 5,134,066; U.S. Pat. No. 5,175,273; U.S. Pat. No. 5,367,066; U.S. Pat. No. 5,432,272; U.S. Pat. No. 5,457,187; U.S. Pat. No. 5,459,255; U.S. Pat. No. 5,484,908; U.S. Pat. No. 5,502, 177; U.S. Pat. No. 5,525,711; U.S. Pat. No. 5,552,540; U.S. Pat. No. 5,587,469; U.S. Pat. No. 5,596,091; U.S. Pat. No. 5,614,617; U.S. Pat. No. 5,750,692, and U.S. Pat. No. 5,681, 941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The inhibitory nucleic acids useful in the present methods are sufficiently complementary to all or part of miR-26a, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a miR-26a sequence, then the bases are considered to be complementary to each other at that position. 100% complementarity is not required.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. The inhibitory nucleic acids and the miR-26a are complementary to each other when a sufficient number of corresponding positions in each molecule are occupied by nucleotides that can hydrogen bond with each other. Thus, "specifically hybridizable" and "complementary" are terms which are used to indicate a sufficient degree of complementarity or precise pairing such that stable and specific binding occurs between the inhibitory nucleic acid and the miR-26a target sequence. For example, if a base at one position of an inhibitory nucleic acid is capable of hydrogen bonding with a base at the corresponding position of a miR-26a molecule, then the bases are considered to be complementary to each other at that position.

Although in some embodiments, 100% complementarity is desirable, it is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target miR-26a molecule interferes with the normal function of the target miR-26a to cause a loss of activity, and there is a sufficient degree of complementarity to avoid non-specific binding of the sequence to non-target miR-26a sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., *Molecular Cloning: A Laboratory Manual*, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within miR-26a (e.g., a target region comprising the seed sequence as described herein). For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Antisense and other compounds of the invention that hybridize to a miR-26a target sequence are identified through routine experimentation. In general the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to a miR-26a target sequence. Thus, oligonucleotides are chosen that are sufficiently complementary to the target, i.e., that hybridize sufficiently well and with sufficient specificity, to give the desired effect.

Modified Bases/Locked Nucleic Acids (LNAs)

In some embodiments, the inhibitory nucleic acids used in the methods described herein comprise one or more modified bonds or bases. Modified bases include phosphorothioate, methylphosphonate, peptide nucleic acids, or locked nucleic acid (LNA) molecules. Preferably, the modified nucleotides are locked nucleic acid molecules, including [alpha]-L-LNAs. LNAs comprise ribonucleic acid analogues wherein the ribose ring is "locked" by a methylene bridge between the 2'-oxygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a miR-26a target sequence. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA (or any other inhibitory nucleic acid described herein); for example, a series of oligonucleotides of 7- or 10-30 nucleotides spanning the length of a target miR-26a sequence can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of three or more Gs or Cs, or more than four LNA residues, should be avoided where possible (for example, it may not be possible with very short (e.g., about 9-10 nt) oligonucleotides). In some embodiments, the LNAs are xylo-LNAs.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

In some embodiments of the methods described herein, the inhibitory nucleic acid is or comprises ACTTGA (SEQ ID NO:5) wherein all of the nucleic acids are locked and the backbone is a phosphorothioate backbone.

Antagomirs

In some embodiments, the antisense is an antagomir. Antagomirs are chemically modified antisense oligonucleotides that target a miR-26a target sequence. For example, an antagomir for use in the methods described herein can include a nucleotide sequence sufficiently complementary to hybridize to a miR-26a target sequence of about 12 to 25 nucleotides, preferably about 15 to 23 nucleotides.

In general, antagomirs include a cholesterol moiety, e.g., at the 3'-end. In some embodiments, antagomirs have various modifications for RNase protection and pharmacologic properties such as enhanced tissue and cellular uptake. For example, In addition to the modifications discussed above for antisense oligos, an antagomir can have one or more of complete or partial 2'-O-methylation of sugar and/or a phosphorothioate backbone. Phosphorothioate modifications provide protection against RNase activity and their lipophilicity contributes to enhanced tissue uptake. In some embodiments, the antagomir can include six phosphorothioate backbone modifications; two phosphorothioates are located at the 5'-end and four at the 3'-end. See, e.g., Krutzfeldt et al., Nature 438, 685-689 (2005); Czech, N Engl J Med 2006; 354:1194-1195 (2006); Robertson et al., Silence. 1:10 (2010); Marquez and McCaffrey, Hum Gene Ther. 19(1):27-38 (2008); van Rooij et al., Circ Res. 103(9):919-928 (2008); and Liu et al., Int. J. Mol. Sci. 9:978-999 (2008). Antagomirs useful in the present methods can also be modified with respect to their length or otherwise the number of nucleotides making up the antagomir. The antagomirs must retain specificity for their target, i.e., must not directly bind to, or directly significantly affect expression levels of, transcripts other than the intended target.

In some embodiments, the inhibitory nucleic acid is locked and includes a cholesterol moiety (e.g., a locked antagomir).

siRNA/shRNA

In some embodiments, the nucleic acid sequence that is complementary to miR-26a can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc Natl Acad Sci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Man, 1995 J. Med. Chem. 38, 2023-2037). Enzymatic nucleic acid molecules can be designed to cleave miR-26a within the background of cellular RNA. Such a cleavage event renders the miR-26a non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261: 1411-1418; Szostak, 1993, TIBS 17, 89-93; Kumar et al, 1995, FASEB J., 9, 1183; Breaker, 1996, Curr. Op. Biotech., 1, 442)

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Inhibitory nucleic acids useful in the methods described herein can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 2010/0004320, US 2009/0298916, and US 2009/0143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning; A Laboratory Manual* 3d ed. (2001); *Current Protocols in Molecular Biology*, Ausubel et al., eds. (John Wiley & Sons, Inc., New York 2010); Kriegler, *Gene Transfer and Expression: A Laboratory Manual* (1990); *Laboratory Techniques In Biochemistry And Molecular Biology: Hybridization With Nucleic Acid Probes, Part I. Theory and Nucleic Acid Preparation*, Tijssen, ed. Elsevier, N.Y. (1993).

Pharmaceutical Compositions

The methods described herein can include the administration of pharmaceutical compositions and formulations comprising inhibitory nucleic acid sequences designed to target miR-26a.

In some embodiments, the compositions are formulated with a pharmaceutically acceptable carrier. The pharmaceutical compositions can be formulated to be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy*, 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations of this invention can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716, 928 describing using essential oils or essential oil components for increasing bioavailability and reducing inter- and intra-individual variability of orally administered hydrophobic pharmaceutical compounds (see also U.S. Pat. No. 5,858, 401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ, or by intracoronary administration. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to decrease serum levels of triglycerides in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; *Remington: The Science and Practice of Pharmacy,* 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as *Remington: The Science and Practice of Pharmacy,* 21st ed., 2005.

Various studies have reported successful mammalian dosing using complementary nucleic acid sequences. For example, Esau C., et al., (2006) Cell Metabolism, 3(2):87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾45, ALT ¾35) for all doses with the exception of the 75 mg/kg dose of miR-122 ASO, which showed a very mild increase in ALT and AST levels. They concluded that 50 mg/kg was an effective, non-toxic dose. Another study by Krützfeldt J., et al., (2005) Nature 438, 685-689, injected antagomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg kg-1 LNA-anti-miR, leading to a long-lasting and reversible decrease in total plasma cholesterol without any evidence for LNA-associated toxicities or histopathological changes in the study animals.

In some embodiments, the methods described herein can include co-administration with other drugs or pharmaceuticals, e.g., compositions for treating an ischemic attack, e.g., TpA. For example, the inhibitory nucleic acids can be co-administered with drugs for treating or reducing risk of a disorder described herein.

Methods of Diagnosis

Included herein are methods for diagnosing of disorders associated with impaired angiogenesis or blood flow to a tissue in the body, e.g., ischemic heart disease, coronary artery disease, ischemic heart failure, peripheral artery disease (PAD), critical limb ischemia, and diabetic foot ulcers. The methods include obtaining a sample from a subject, and evaluating the presence and/or level of miR-26a in the sample, and comparing the presence and/or level with one or more references, e.g., a control reference that represents a normal level of miR-26a, e.g., a level in an unaffected subject, and/or a disease reference that represents a level of the proteins associated with miR-26a, e.g., a level in a subject having a disorder associated with impaired angiogenesis or blood flow to a tissue in the body as described herein. The presence and/or level of miR-26a can be evaluated using methods known in the art, e.g., Northern blot, RNA expression assays, e.g., microarray analysis, RT-PCR, deep sequencing, cloning, and quantitative real time polymerase chain reaction (qRT-PCR). Analytical techniques to determine RNA expression are known. See, e.g., Sambrook et al., *Molecular Cloning: A Laboratory Manual,* 3rd Ed., Cold Spring Harbor Press, Cold Spring Harbor, N.Y. (2001). In some embodiments, high throughput methods, e.g., gene chips as are known in the art (see, e.g., Ch. 12, Genomics, in Griffiths et al., Eds. Modern genetic Analysis, 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect the presence and/or level of miR-26a.

In some embodiments, the presence and/or level of miR-26a is comparable to the presence and/or level of miR-26a in the disease reference, and the subject has one or more symptoms associated with disorders associated with impaired angiogenesis or blood flow to a tissue in the body, e.g., ischemic heart disease, coronary artery disease, ischemic heart failure, peripheral artery disease (PAD), critical limb ischemia, and diabetic foot ulcers, then the subject has the disorder, e.g., can be diagnosed with the disorder using a method described herein. In some embodiments, the subject has no overt signs or symptoms of disorders associated with impaired angiogenesis or blood flow to a tissue in the body, but the presence and/or level of miR-26a is comparable to the presence and/or level of miR-26a in the disease reference, then the subject has an increased risk of developing a disorder associated with impaired angiogenesis or blood flow to a tissue in the body, e.g., ischemic heart disease, coronary artery disease, ischemic heart failure, peripheral artery disease (PAD), critical limb ischemia, and diabetic foot ulcers. In some embodiments, the sample includes a biological fluid, e.g., blood, serum, plasma, saliva, and/or urine. In some embodiments, once it has been determined by a method described herein that a person has a disorder associated with impaired angiogenesis or blood flow to a tissue in the body, e.g., ischemic heart disease, coronary artery disease, ischemic heart failure, peripheral artery disease (PAD), critical limb ischemia, or diabetic foot ulcers, or has an increased risk of developing such a disorder, then a treatment, e.g., as known in the art or as described herein, can be administered.

Suitable reference values can be determined using methods known in the art, e.g., using standard clinical trial methodology and statistical analysis. The reference values can have any relevant form. In some cases, the reference comprises a predetermined value for a meaningful level of miR-26a, e.g., a control reference level that represents a normal level of miR-26a, e.g., a level in an unaffected subject or a subject who is not at risk of developing a disease described herein, and/or a disease reference that represents a level of the proteins associated with conditions associated with reduced or impaired angiogenesis or blood flow to a tissue in the body or endothelial progenitor cell dysfunction, e.g., a level in a subject having one or more disorders associated with impaired angiogenesis or blood flow to a tissue in the body, e.g., ischemic heart disease, coronary artery disease, ischemic heart failure, peripheral artery disease (PAD), critical limb ischemia, and/or diabetic foot ulcers.

The predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

In some embodiments, the predetermined level is a level or occurrence in the same subject, e.g., at a different time point, e.g., an earlier time point.

Subjects associated with predetermined values are typically referred to as reference subjects. For example, in some embodiments, a control reference subject does not have a disorder described herein (e.g., disorders associated with impaired angiogenesis or blood flow to a tissue in the body, e.g., ischemic heart disease, coronary artery disease, ischemic heart failure, peripheral artery disease (PAD), critical limb ischemia, and/or diabetic foot ulcers). In some cases it may be desirable that the control subject is a diabetic (e.g., a diabetic who does not have vascular complications), and in other cases it may be desirable that a control subject is a non-diabetic.

A disease reference subject is one who has (or has an increased risk of developing) one or more disorders associated with impaired angiogenesis or blood flow to a tissue in the body, e.g., ischemic heart disease, coronary artery disease, ischemic heart failure, peripheral artery disease (PAD), critical limb ischemia, and/or diabetic foot ulcers. An increased risk is defined as a risk above the risk of subjects in the general population.

Thus, in some cases the level of miR-26a in a subject being less than or equal to a reference level of miR-26a is indicative of a clinical status (e.g., indicative of a disorder as described herein, e.g., disorders associated with impaired angiogenesis or blood flow to a tissue in the body, e.g., ischemic heart disease, coronary artery disease, ischemic heart failure, peripheral artery disease (PAD), critical limb ischemia, and/or diabetic foot ulcers). In other cases the level of miR-26a in a subject being greater than or equal to the reference level of miR-26a is indicative of the absence of disease or normal risk of the disease. In some embodiments, the amount by which the level in the subject is the less than the reference level is sufficient to distinguish a subject from a control subject, and optionally is a statistically significantly less than the level in a control subject. In cases where the level of miR-26a in a subject being equal to the reference level of miR-26a, the "being equal" refers to being approximately equal (e.g., not statistically different).

The predetermined value can depend upon the particular population of subjects (e.g., human subjects) selected. For example, an apparently healthy population will have a different 'normal' range of levels of miR-26a than will a population of subjects which have, or are likely to have, a disorder described herein. Accordingly, the predetermined values selected may take into account the category (e.g., sex, age, health, risk, presence of other diseases) in which a subject (e.g., human subject) falls. Appropriate ranges and categories can be selected with no more than routine experimentation by those of ordinary skill in the art.

In characterizing likelihood, or risk, numerous predetermined values can be established.

EXAMPLES

The invention is further described in the following examples, which do not limit the scope of the invention described in the claims.

Materials and Methods

The following Materials and methods were used in the Examples set forth herein.

Cell Culture

Human umbilical vein endothelial cells (cc-2159; Lonza, Walkersville, Md.) were cultured in growth media EGM®-2 (cc-3162; Lonza Walkersville, Md.) per manufacturer's instructions. Cells were passaged 2 times before being treated with TNF-α, TGF-β or BMP-2 (R&D Systems) for 24 hours. Samples were collected from 3 separate lots per experiment.

MicroRNA and Total RNA Preparation, Quantitative Reverse-Transcription PCR

Total RNA and microRNA was isolated using Trizol® reagent (Invitrogen) per manufacturer's instructions. RNA was quantitated using μ Quant (Bio-Tech Instruments Inc). For qPCR analysis, RNA was converted to cDNA using miScript Reverse Transcriptase kit (218061; Qiagen). SYBR Green Assay (218073; Qiagen) was used for quantitative real-time qPCR analysis with the Mx3000P Real-time PCR system (Strategene). To amplify mature miRNA sequences, miScript primer assays for Hs_RN5S1_1 (MS00007574), Hs_miR-26a_1 (MS00006559), Hs_miR26b_1 (MS00003234) from Qiagen were used. Samples were normalized to endogenous 5S RNA (human). Fold changes were calculated by ΔΔCt method.

MicroRNA Array Analysis

RNA samples collected by Trizol reagent (Invitrogen) were pooled by treatment group and array analysis was performed by LC Sciences. For each group, 3 replicates were collected. Array results were confirmed for miR-26a by qRT-PCR.

Targeted miRNA Overexpression and Inhibition

HUVECs were plated at 50,000 cells/well and cultured overnight before being transfected with Lipofectamine™ 2000 transfection reagent (Invitrogen) was used for transfection, following manufacturer's instructions. MiR-26a was overexpressed in HUVECs using 30 nM of hsa-miRNA-26a Pre-miR™ miRNA Precursor oligo (AM17100) in parallel with Cy™3 labeled-negative control #1 (AM17120; Ambion). Inhibition of miR-26a was achieved by 100 nm of hsa-miRNA-26a inhibitor oligo (AM17000, Ambion) in parallel with Cy3 labeled negative control (AM17011; Ambion).

Luciferase Reporter Assays

HUVECs were plated (50000/well) in triplicate on a 12-well plate. After growing to 70-80% confluency, cells were transfected with 800 ng of the indicated reporter constructs and 200 ng β-galactosidase (β-gal) expression plasmids. MiR-26a mimics or inhibitors or non-specific controls were co-transfected at 30 or 100 nM final concentration where indicated. Transfected cells were collected in 200 μl Reporter Lysis Buffer (Promega). The activity of luciferase and β-gal were measured. Each reading of luciferase activity was normalized to the β-gal activity read for the same lysate.

ELISA:

HUVECs were plated at 50,000 cells/well overnight, transfected with miR-26a mimics or inhibitors or non-specific controls and the supernatant was collected from each well. For each group, 3 technical replicates were collected. The supernatants were examined by ELISA analysis by means of SearchLight MultiPlex Immunoassay Kit (Aushon Biosystems, Inc).

Tube Like Network Formation on Matrigel (In-Vitro and In-Vivo)

Matrigel (BD Bioscience) basement membrane matrix was added to 96 well culture plates and incubated at 37° C. until gelation occurred. HUVECs transfected with miR-26a mimic or miR-26a inhibitor were cultured for 72 hours before being plated on Matrigel at 20,000 cells/well. Network tube formation was assessed 14 hours post-plating and quantitated by counting the number of tubes formed per high power field. 6 technical replicated were used per condition. For in-vivo angiogenesis assay, HUVECs transfected with miR-26a mimic, miR-26a inhibitor, or non-specific negative controls were cultured for 72 hours before admixed with Matrigel ($1*10^6$ cells/ml), bFGF (250 ng per mL, R&D Systems), and heparin (60 units per mL; Hospira, Inc.). Matrigel plugs (n=5) admixed with transfected HUVECs were implanted subcutaneously into nude mice and collected 7 days post implantation. Angiogenesis in matrigel plugs was analyzed using human CD31 Ab staining of the paraffin embedded matrigel sections.

Chemotaxis Assays

Migration assay was performed using ChemTX multiwell system (Neuro probe Inc, MD) with 5 mm pore size and 96 well format. HUVECs transfected with miR-26a mimic or miR-26a inhibitor were cultured for 72 hours before being plated on the upper compartment of the multiwell plate to assess migration. Lower compartments were filled with EBM-2 medium containing TNF-α, BMP-2 or VEGF (R&D Systems). The number of cells migrating to the lower chamber was counted using a hemocytometer after 5 hours. Three technical replicated were used per condition and studies were validated in at least 2 independent experiments.

Western Blots Analysis

HUVECs transfected with miR-26a mimic or miR-26a inhibitor were cultured for 72 hours. Total cellular protein was isolated by RIPA buffer (50 mM Tris-HCL pH 7.4, 150 mM NaCl, 1% NP-40, 0.5% sodium deoxycholate, 0.1% SDS) supplemented with protease inhibitors (Roche). Cell or tissue debris was removed by centrifugation at 12000 rpm for 10 min. Lysates were separated by 8% or 10% SDS-PAGE gels, transferred to PVDF membranes (Bio-Rad). Protein quantification was performed using the BCA kit (Thermo Scientific) and cellular lysates were subjected to Western blotting using antibodies against SMAD1 (Cell Signaling), SMAD2 (Abcam), SMAD4 (Cell Signaling), SMAD7 (Abcam), Id1 (Abcam) p21 (Cell Signaling), p27 (Cell Signaling), Cyclin D2 (Cell Signaling), Cyclin E2 (Cell Signaling), and β-actin (Cell Signaling). HRP-conjugated goat anti-rabbit or mouse antibody (Santacruz) was used at 1:5000 dilution. ECL assay was performed per manufacturer's instructions (RPN2132; GE Healthcare).

Mouse LAD-Ligation, MI Model

Animal protocols were approved by the Laboratory Animal Care at Harvard Medical School. Male, 8-10 weeks old, C57/B6 mice (Charles River) (n=11-12/group) were used to tail-vein inject either scrambled control oligo or antagomir-26a (Exiqon) at 24 mg/kg. Twenty-four hrs later these mice underwent acute myocardial infarction (MI) consisting of 45 minutes of left anterior descending artery (LAD) ligation 24 hours post-tail vein injections. Mice were euthanized 24 hours post-surgery and blood, aorta and hearts were harvested. Angiogenesis in heart was analyzed by mouse CD31 staining and isolectin B4 (B-1205; Vector) of the paraffin embedded heart sections. Fluorescent images were acquired by Olympus Fluoview FV1000 confocal microscope.

Circulating miR-26a Levels in Patients with Acute Coronary Syndromes

Patient plasma samples were collected, and RNA was isolated from the plasma using methods as described by Norgen, Inc and qPCR for miR-26a was performed as detailed above. Control patients were defined as without clinically significant coronary atherosclerosis (<20% stenosis in any epicardial coronary artery determined by angiography) and patients with acute coronary syndromes were defined as acute atherothrombotic coronary artery occlusion resulting in either an NSTEMI (with >70% occlusion of an epicardial artery) or an STEMI (complete occlusion of an epicardial coronary artery determined by angiography).

Statistical Analysis

Data are presented as mean±SEM. All in vitro experiments are representative of 3 independent experiments. Data were subjected to Student's t-test and p<0.05 was considered statistically significant. Human data was analyzed by the Mann-Whitney U test.

Example 1

Figure 1A:
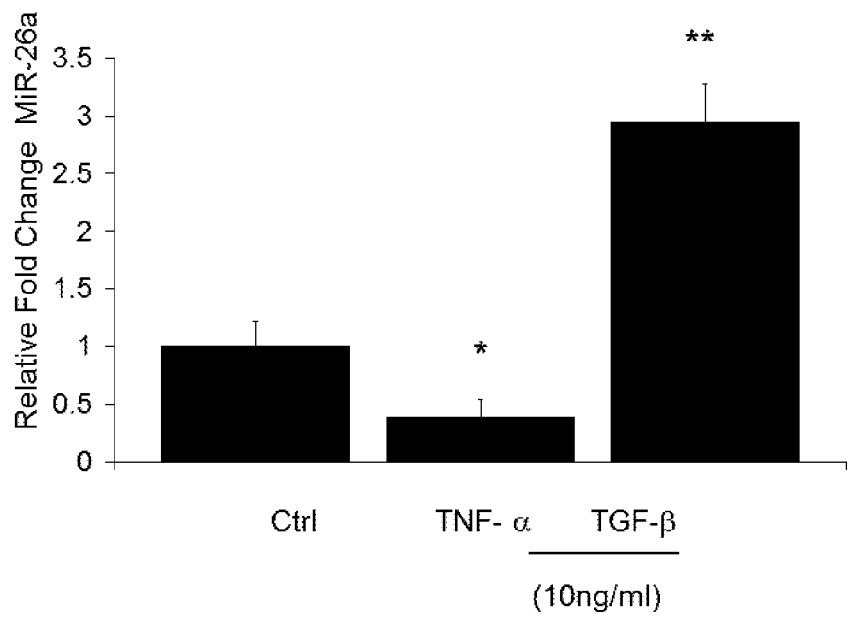
FIGS. 1A-G. MiR-26a is differentially regulated by pro-angiogenic stimuli in HUVECs and regulates cell growth, cell cycle, migration, and network formation in HUVECs. RNA was extracted from treated and untreated HUVECs and subjected to microRNA array analysis. (A) Expression of miR-26a was confirmed by RT-qPCR analysis of HUVECs treated with TNF-α or TGF-β for 24 hours and was compared with untreated controls. *, p<0.001 vs ctrl; **p<0.001 vs ctrl (B) Expression of miR-26a and miR-26b were confirmed by RT-qPCR analysis of HUVECs. HUVECs were transfected with miR-26a$_m$ to overexpress miR-26a or miR-26a$_i$ to inhibit miR26a expression. A scrambled control oligo was transfected in parallel. (C) Number of cells were counted on days 0, 2, 3, and 4. Results are representative of n=6 replicates. *, p<0.001 (D) Tube-like network formation in-vitro (n=6 replicates/condition). *, p<0.001 (E) Effect of miR-26a on cell migration in-vitro (n=3 replicates/condition). Table 1: Transfected HUVECs were subjected to PI staining and FACS analysis. Results are representative of n=3 experiments. *, p<0.001 (F) RNA was extracted from HUVECs that were untreated or treated with BMP2 for 24 hrs. Expression of miR-26a was detected by RT-qPCR analysis; *, p<0.001. (G) VEGF release from HUVECs in response to miR-26a overexpression or inhibition. Supernatants from transfected cells were pooled (n=3) and subjected to ELISA assay; *, p<0.05.
Figure 1B:
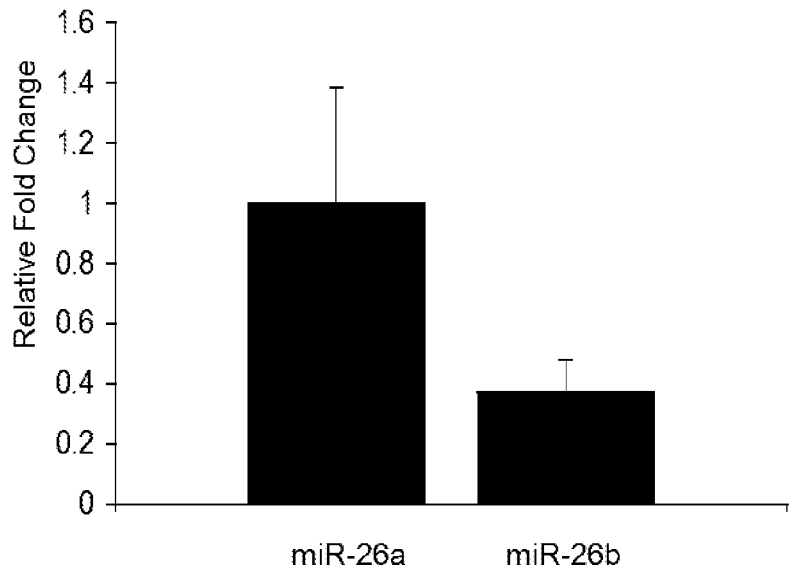
Figure 1C:
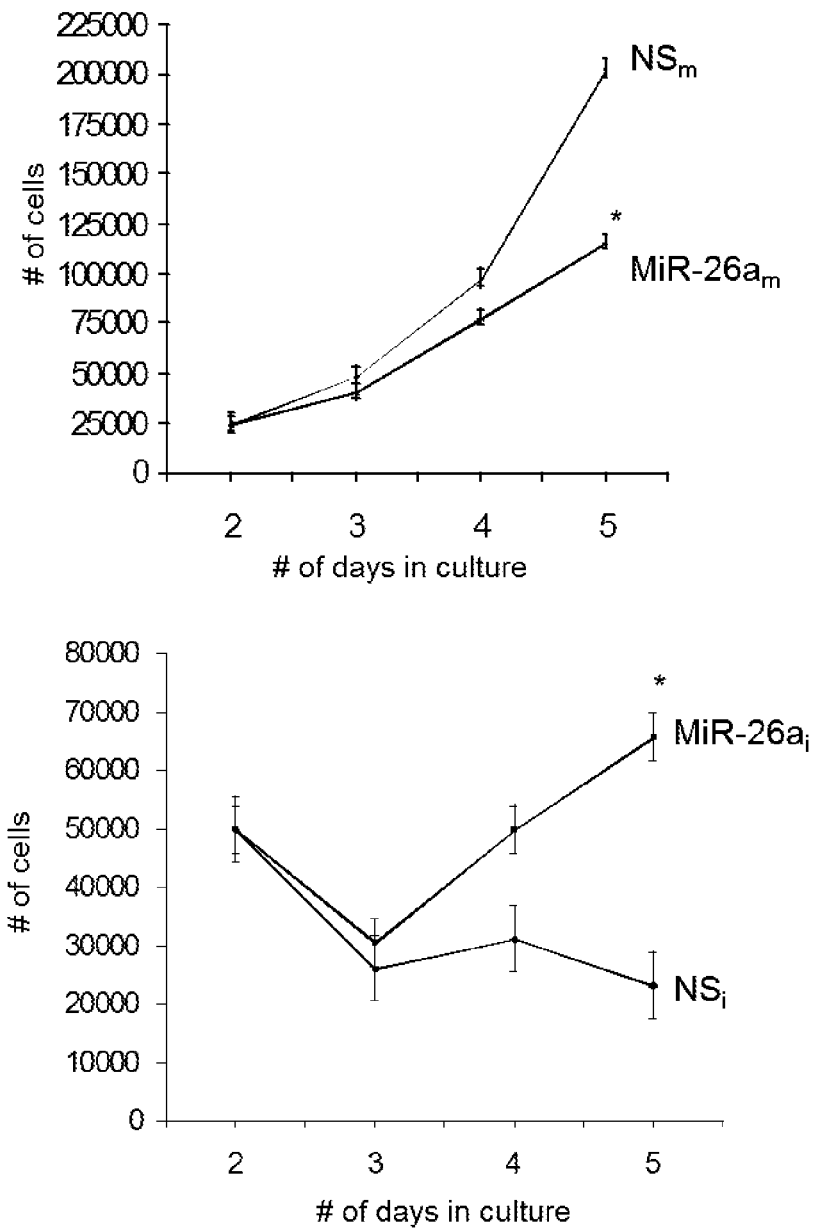
Figure 1D:
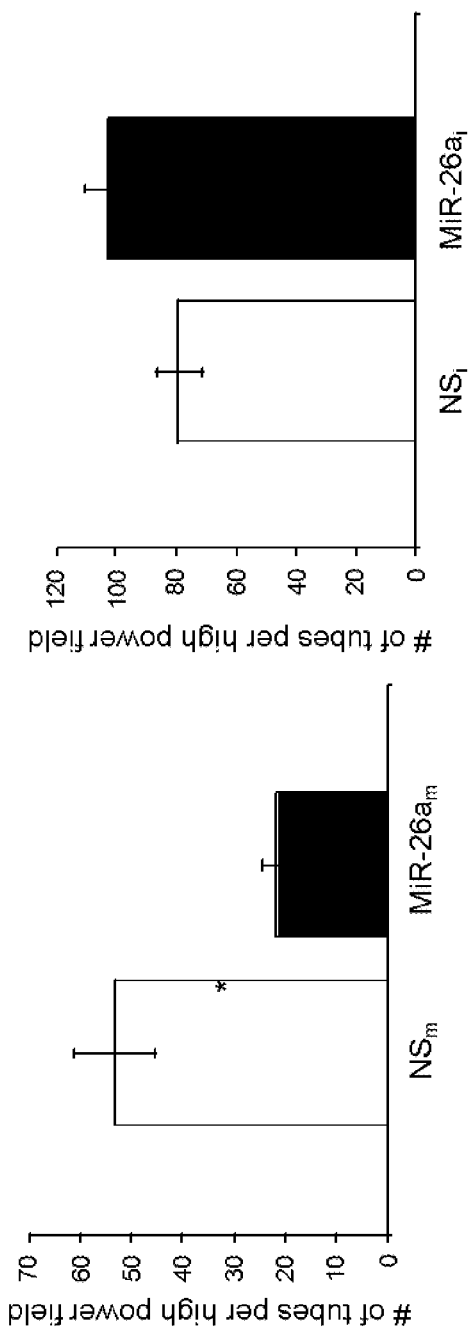
Figure 1E:
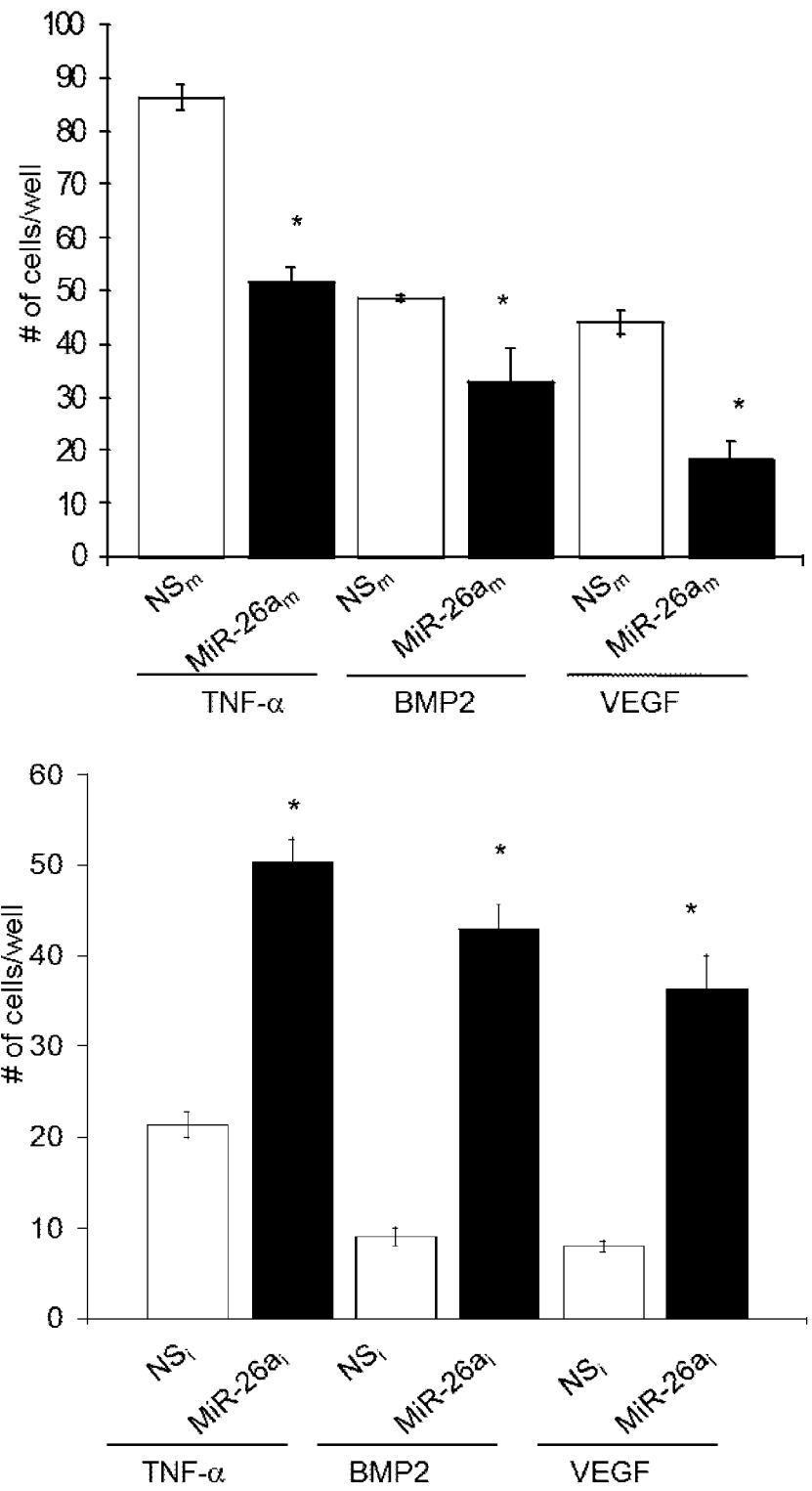
Figure 1F:
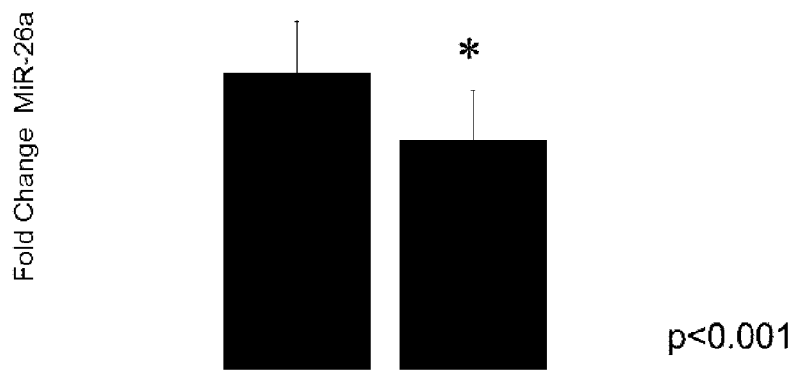

MiR-26a is Expressed in HUVECs and Differentially Regulated by Pro-Angiogenic Stimuli To identify microRNAs that may regulate angiogenesis, microRNA microarray analyses were performed comparing HUVECs treated in the presence or absence of TNF-α for 24 hrs and yielded 33 differentially regulated miRs. Of these 33 miRs, miR-26a was among the most differentially regulated-TNF-α stimulation repressed miR-26a expression by ~25%. To verify the results of microRNA microarray analysis, qPCR analysis was performed. HUVECs were treated with TNF-α in a similar manner and miR-26a expression was reduced by 70% (FIG. 1A). BMP2 also decreased miR-26 expression by 20% (FIG. 1F). In addition to TNF-α, HUVECs were treated with the pleiotropic growth factor transforming growth factor (TGF-β). In contrast, TGF-β1 treatment, which can act as a cell growth inhibitor, increased miR-26a expression by 2.92 fold (FIG. 1A). MiR-26a belongs to the miR-26 family, which is comprised of miR-26a and miR-26b. The expression of miR-26a was ~3 fold higher than miR-26b, suggesting that miR-26a is the dominant family member expressed in HUVECs (FIG. 1B).

Example 2

MiR-26a Regulates Growth and Angiogenic Functional Properties of HUVECs

Because miR-26a was differentially regulated by antagonistic angiogenic stimuli, its functional role in EC growth was studied. Cells transfected with pre-miR precursor-26a (miR-26a$_m$), showed significantly decreased growth (by 1.8 fold) compared to the cells transfected with the NS control oligo. In contrast, cells transfected with antagomiR-26a, which inhibits miR-26a (miR-26a$_i$), showed increased growth (by 2.8 fold) of HUVECs (FIG. 1C). Next the transfection efficiency of HUVECs was examined by using Cy3-labeled oligos and achieved over 95% transfection efficiency. In accordance with the decreased cell growth properties in response to miR-26a, FACS analyses of cells transfected with miR-26a$_m$ showed marked cell cycle arrest (76% vs. 61%, respectively) at the G1 phase compared to the NS control transfected HUVECs. Conversely, inhibition of miR-26a resulted in cell cycle progression of HUVECs with a decreased number of cells (56% vs. 65%, respectively) in the G1 phase (Table 1).

TABLE 1

|    | NS$_m$ | MiR-26a$_m$ | NS$_i$ | MiR26a$_i$ |
|----|--------|-------------|--------|------------|
| G1 | 61.3 ± 6.1 | 76 ± 1.4 | 65.2 ± 0.74 | 56.4 ± 3.1 |
| S1 | 21.9 ± 2.7 | 18.1 ± 3.1 | 14.3 ± 3.6 | 20.8 ± 1 |
| G2 | 16.8 ± 5.5 | 5.9 ± 3.3 | 20.2 ± 3.2 | 23.4 ± 4.1 |

*p < 0.01 vs NS$_{mimic}$ or NS$_{inhibitor}$

Figure 1G:
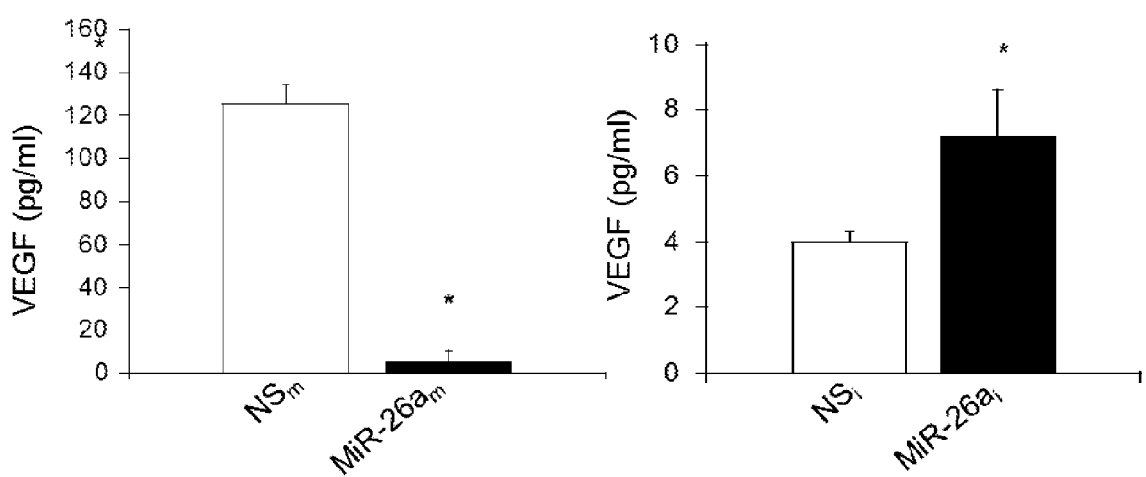

To further characterize the role of miR-26a in HUVECs, vascular network formation was evaluated in matrigel assays. As shown in FIG. 1D, overexpression of miR-26a inhibited network tube formation in matrigel (by 2.5 fold), whereas inhibition of miR-26a significantly increased tube formation (by 1.3 fold). In addition, overexpression of miR-26a decreased EC migration in response to pro-angiogenic stimuli TNF-α, BMP2, and VEGF (by 1.7, 1.5, and 2.4 fold, respectively) compared to the non-specific control. On the other hand, inhibition of miR-26a potently increased migration by 4.5 fold for VEGF and BMP2 treatments and by 2.4 fold for TNF-α treatment compared to the non-specific control (FIG. 1E). Finally, HUVECs overexpressing miR-26a showed decreased levels of the pro-angiogenic factor VEGF, whereas inhibition of miR-26a resulted in increased VEGF release compared to NS control (FIG. 1G). Taken together, these data indicate that miR-26a may potently reduce endothelial cell growth and induce cell growth arrest, effects that may involve critical signaling pathways implicated in angiogenesis.

Example 3

MiR-26a Targets SMAD1 Expression

Figure 2A:
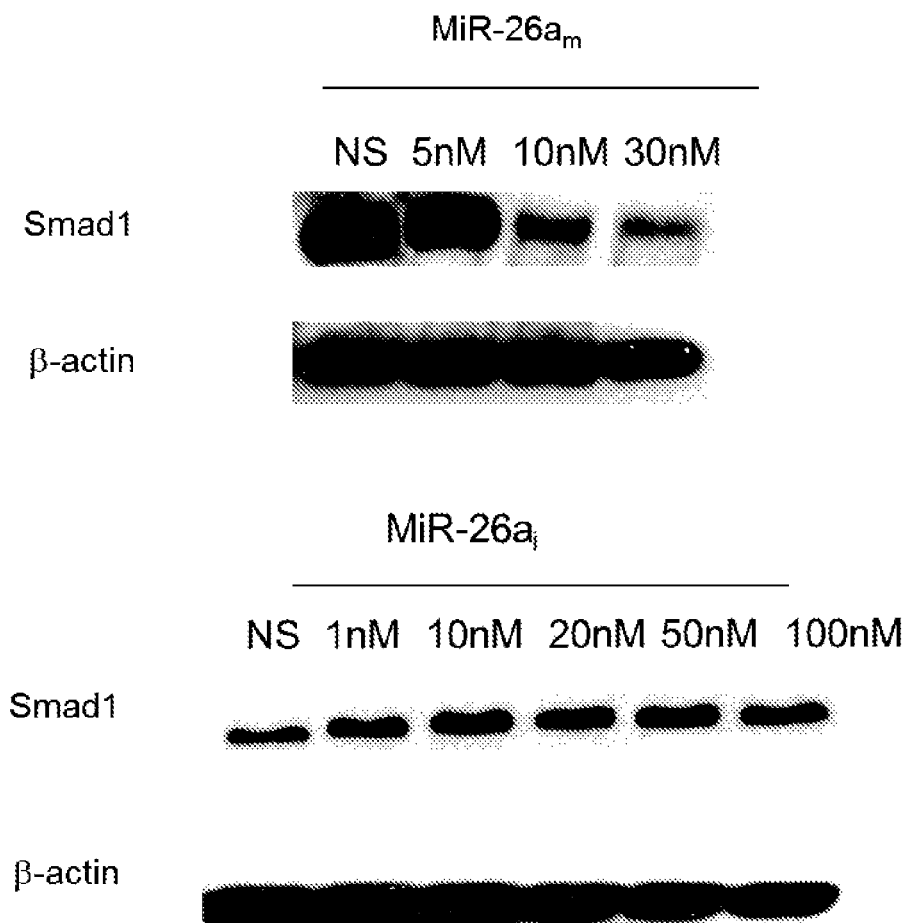
FIGS. 2A-N. MiR-26a targets SMAD1 and regulates downstream targets of the SMAD1 signaling pathway. HUVECs were transfected with miR-26a$_m$ to overexpress miR-26a or miR-26a$_i$ to inhibit miR-26a expression in parallel with the scrambled control. (A-B) Protein expression of SMAD family members in HUVECs was determined by Western blotting using antibodies to SMAD1, SMAD2, SMAD4, SMAD7, and β-actin (n=3 to 5 experiments). (C) Luciferase activity of SMAD1-3'UTR normalized to β-Gal measured in HUVECs transfected with miR-26a$_m$ or miR-26a$_i$ (D) or stimulated with TNF-α or TGF-β for 24 hours (n=3 experiments); *, p<0.05. (E) RNA was harvested from MiR-26a$_m$ or scrambled control transfected cells and lysates were subjected to RNA-immunoprecipitation using antibodies to Ago-myc and GAPDH. RT-qPCR was performed to detect SMAD1; *, p<0.05. (F-G) HUVECs were transfected with SMAD1 siRNA in parallel with the scrambled control to inhibit SMAD1 expression. (F) Protein expression in HUVECs determined by Western blotting using antibodies to SMAD1, p21 and β-actin (n=2 experiments) 72 hours post-transfection. (G) Tube-like network formation in-vitro (n=6 replicates/condition) measured 72 hours post-transfection; *, p<0.05. (H) Number of cells were counted on days 0, 2, 3, 4 and 5. Results are representative of n=3 replicates. Increasing doses of the miR-26a$_m$ to overexpress miR-26a or the miR-26a$_i$ to inhibit miR26a expression in HUVECs is compared to the scrambled control; *, p<0.05. (I) Protein expression in HUVECs determined by Western blotting using antibodies to Id1, p21, p27, SMAD1, and β-actin (n=3 to 5 experiments). (J) Luciferase activity of the Id1 promoter normalized to β-Gal measured in HUVECs overexpressing miR-26a (n=3 experiments); *, p<0.001. HUVECs transfected with miR-26a mimic or inhibitor were cultured for 24 hrs and harvested for FACS to detect (K) Caspase 3 or (L) Annexin IV levels. (M) Luciferase activity of SMAD1-3'UTR normalized to β-Gal measured in HUVECs transfected with miR-26a$_m$ or miR-26a$_i$ stimulated with BMP2 for 24 hours (n=3 experiments) (N) MiR-26a does not target Cyclin D2 or Cyclin E2 in HUVECs. HUVECs were transfected with miR-26a$_m$ to overexpress miR-26a in parallel with the scrambled control. Protein expression in HUVECs determined by Western blotting using antibodies to Cyclin D2, Cyclin E2, and β-actin (n=3 to 5 experiments).
Figure 2B:
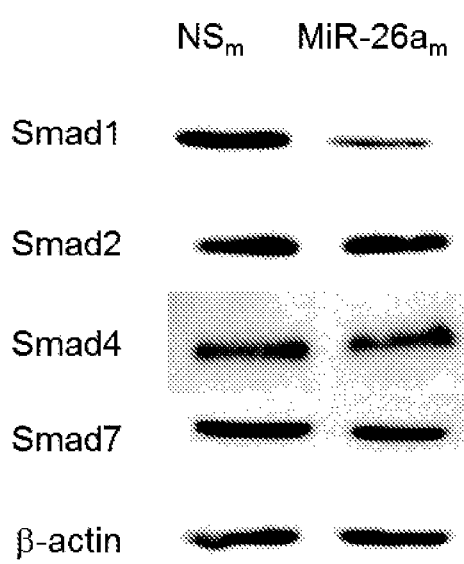
Figure 2C:
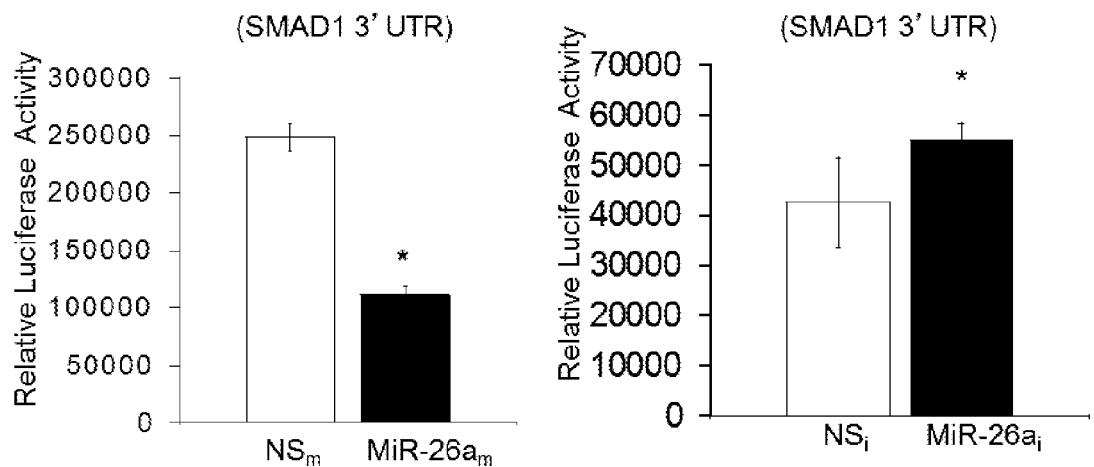
Figure 2D:
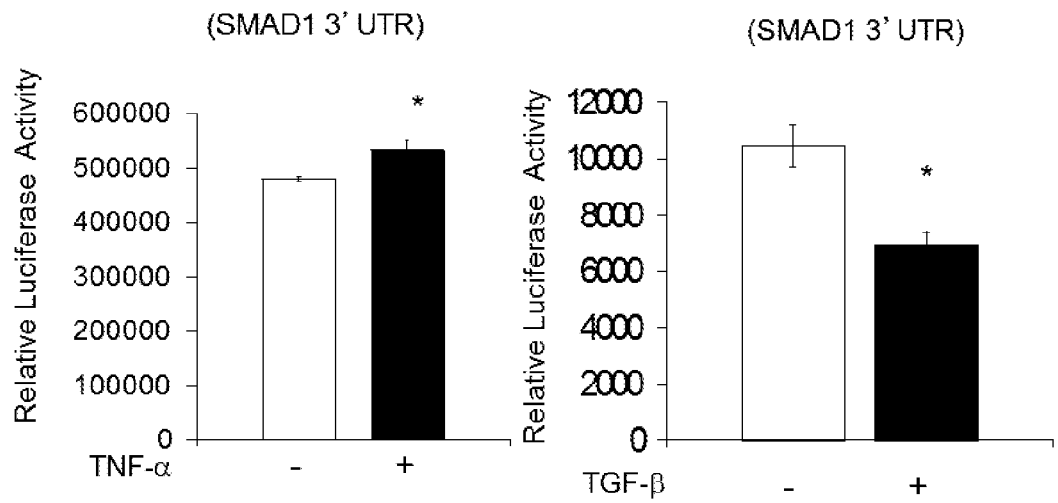
Figure 2E:
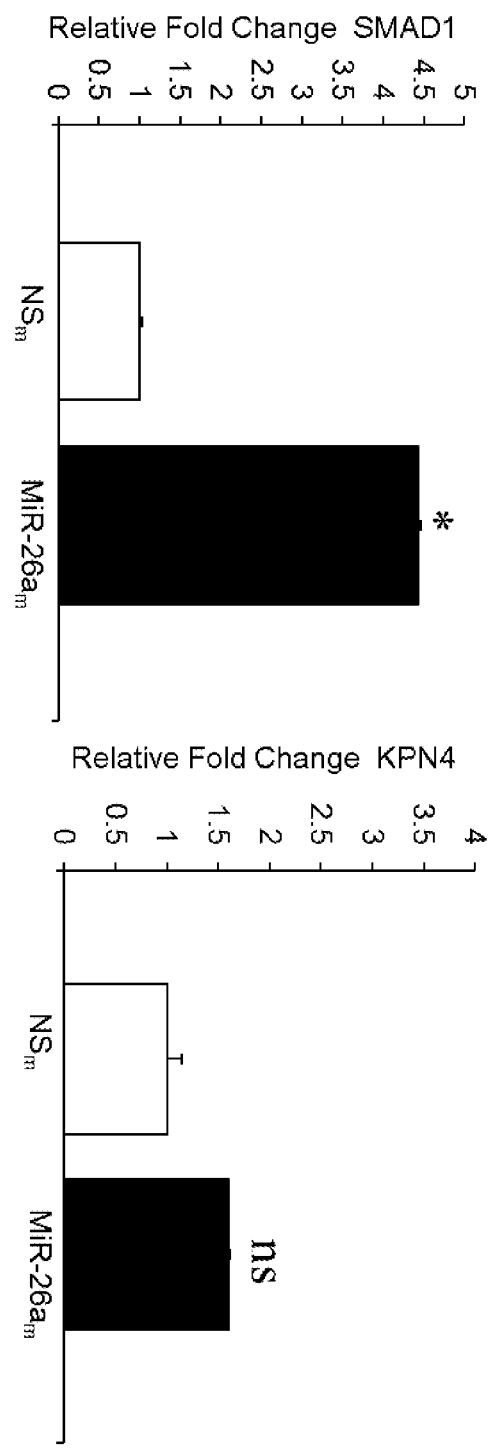
Figure 2F:
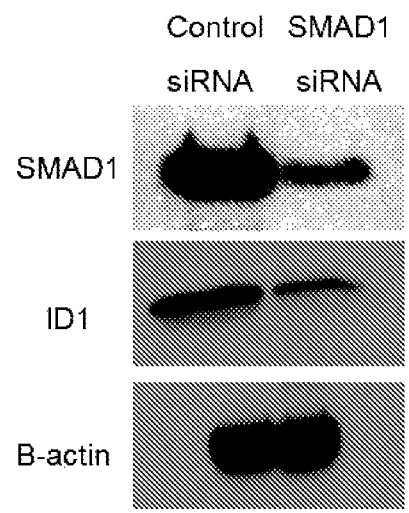
Figure 2G:
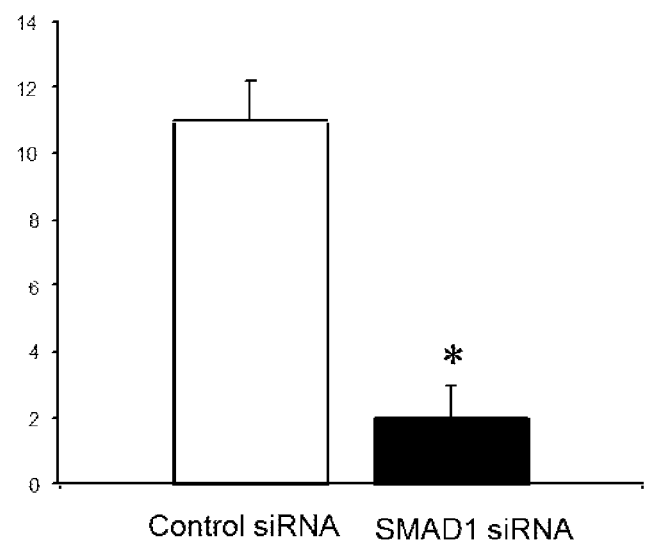
Figure 2H:
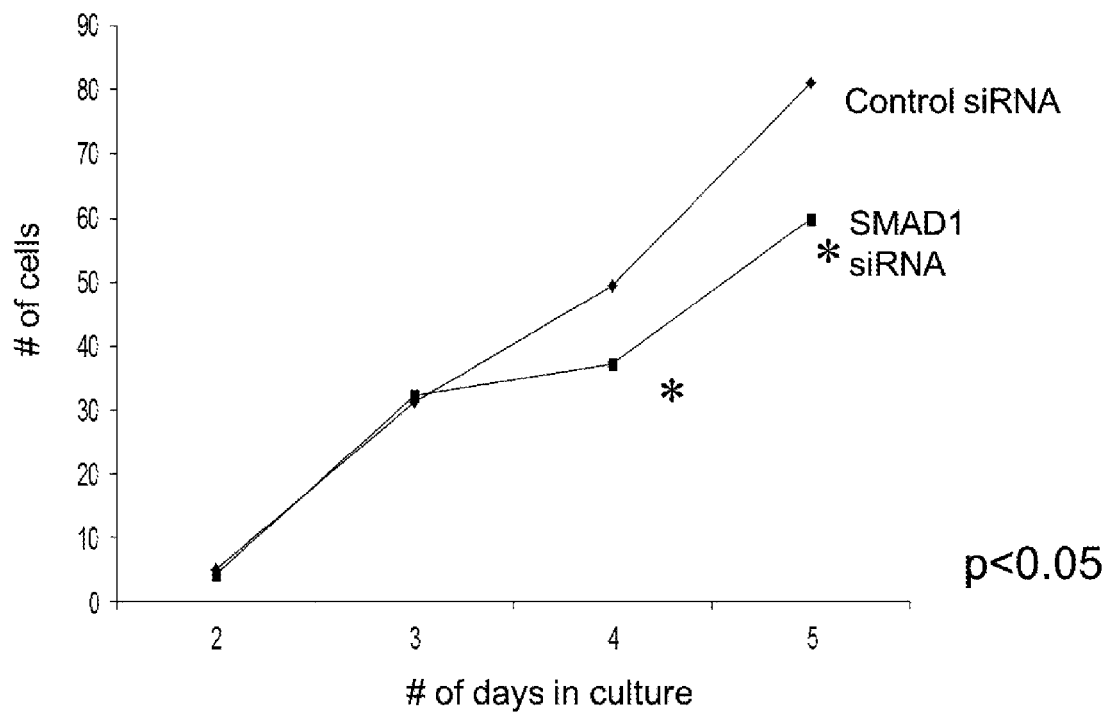
Figure 2I:
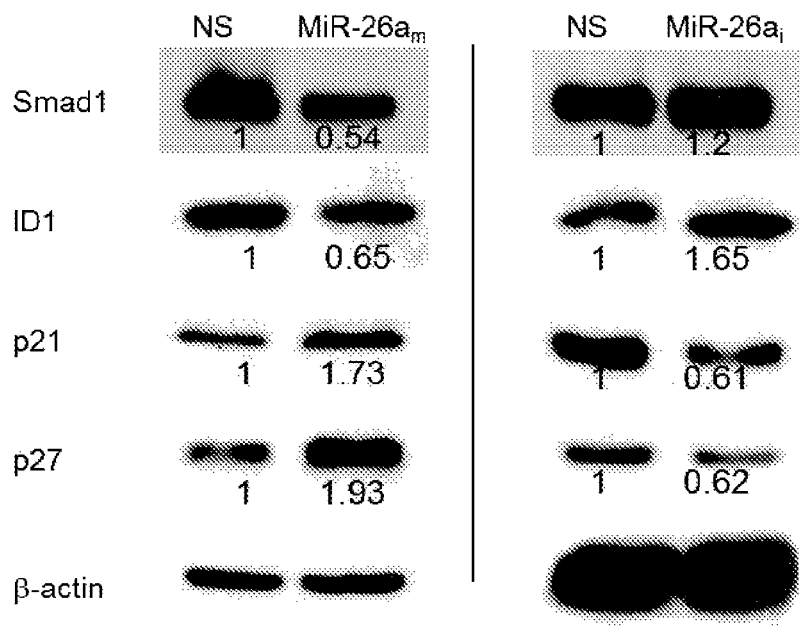
Figure 2J:
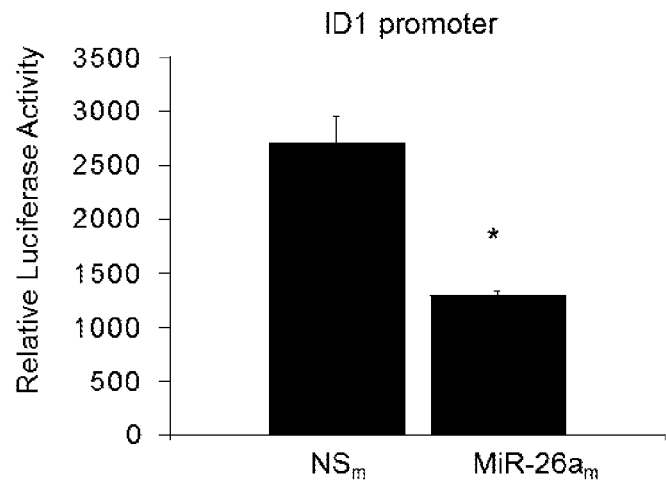
Figure 2K:
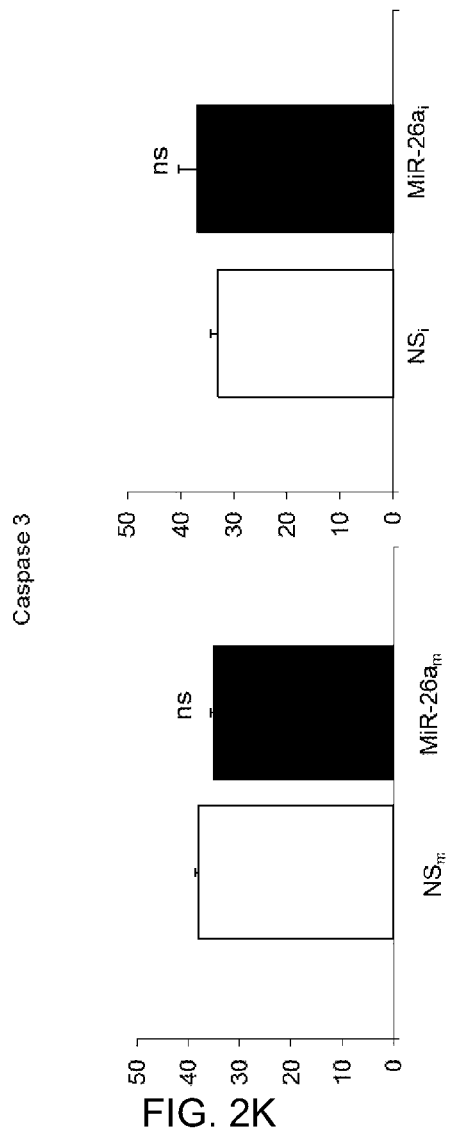
Figure 2L:
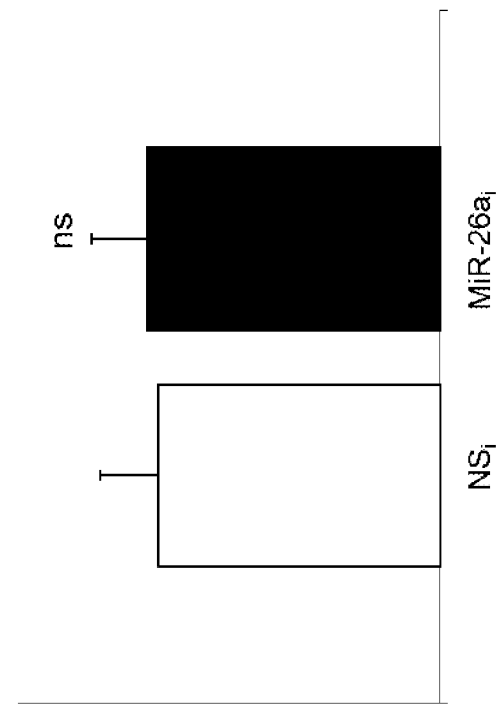
Figure 2L:
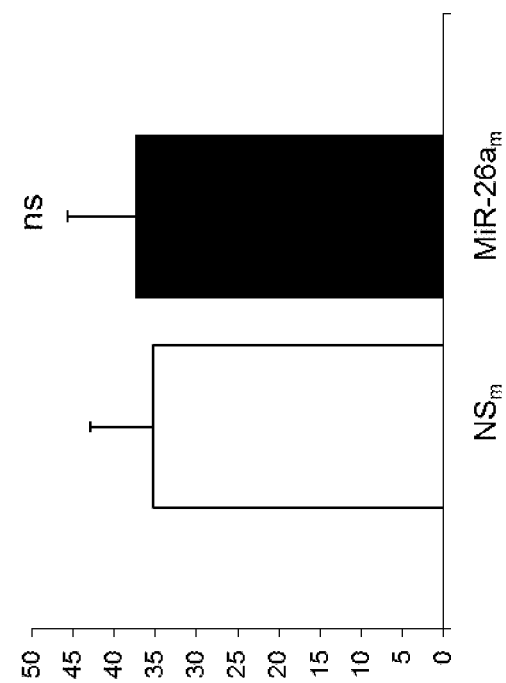
Figure 2M:
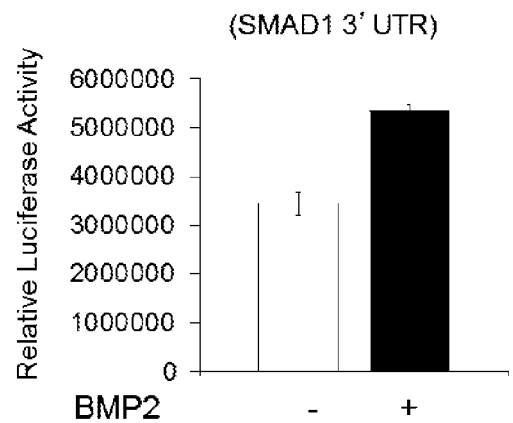

Taking an in silico bioinformatics approach, potential miR-26a targets were analyzed by TargetScan, miRbase and miRanda databases. All 3 databases predicted SMAD1 as a common target of miR-26a with the occurrence of 2 binding sites for miR-26a present in the 3'UTR of the SMAD1 gene. SMAD1 protein levels were significantly reduced (by 6.2 fold) in HUVECs overexpressing miR-26a. Furthermore, inhibition of miR-26a increased (by 1.7 fold) SMAD1 protein levels compared to NS control transfected cells (FIG. 2A). Transfection of HUVECs with the mimic or inhibitors did not cause apoptosis (FIGS. 2K and 2L). In addition, this regulation was specific to SMAD1 and not other Smad family members including Smad2, Smad4 or Smad7 (FIG. 2B). To determine if miR-26a could directly bind to the 3'-UTR of the SMAD1 gene, transfection reporter studies were performed. HUVECs were co-transfected with the SMAD1 3'-UTR and either miR-26a$_m$, miR-26a$_i$, or non-specific controls. As shown in FIG. 2C, overexpression of miR-26a decreased SMAD1 reporter gene activity (by 2.7 fold), whereas inhibition of miR-26a increased SMAD1 reporter activity (by 1.3 fold). Consistent with the above observations, stimuli that decreased endogenous miR-26a in HUVECs such as TNF-α increased SMAD1 3'-UTR reporter activity. TGF-13, which increased endogenous miR-26a, decreased SMAD1 3'-UTR reporter activity (FIG. 2D). Similar to TNF-α, BMP2 also increased SMAD1 3'-UTR reporter activity (FIG. 2M). To further verify that miR-181b directly targets Smad1, Argonaute2 (AGO2) microribonucleoprotein immunoprecipitation (miRNP-IP) studies were performed to assess whether Smad1 mRNA is enriched in the RNA-induced silencing complex following miR-26a overexpression. An approximately 5-fold enrichment of Smad1 mRNA was observed after AGO2 IP in the presence of miR-26a, as compared to that with the miRNA negative control (FIG. 2E). In contrast, AGO2 IP did not enrich the mRNA for importin-a3, a gene that was not predicted to be a miR-26a target (FIG. 4E). To verify the role of SMAD1 as a target of miR-26a, SMAD1 was silenced using siRNA and inhibition of SMAD1 decreased ID1 (FIG. 2F). In addition a similar functional effect to miR-26a was observed where inhibition of SMAD1 decreased the network tube formation (FIG. 2G) as well as decreasing the growth of HUVECs (FIG. 2H). Collectively, these data suggest that miR-26a may be a 'molecular switch' in which in response to pro-angiogenic stimuli, such as TNF- α, reduced levels of miR-26a allow for increased Smad1 expression, thereby facilitating endothelial cell growth and angiogenesis.

Example 4

MiR-26a Regulates a Smad1-Id1-p21/p27 Signaling Pathway in HUVECs

Figure 2N:
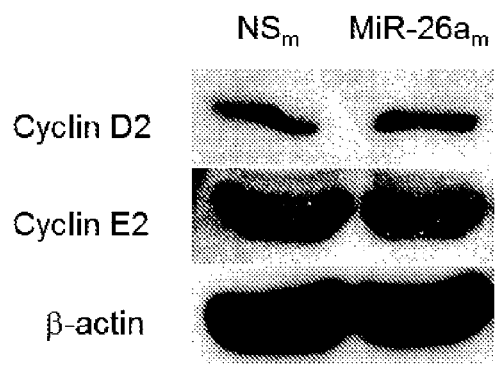

The downstream signaling consequences of miR-26a-mediated repression of Smad1 expression was examined in endothelial cells. Id1 has been identified as a downstream target of the BMP/Smad1 signaling pathway. Id1, a helix-loop-helix protein, acts as a dominant-negative and is known to inhibit the cell cycle inhibitors $p21^{WAF/CIP1}$ or p27 in ECs. Overexpression of miR-26a decreased Id1 expression and increased $p21^{WAF/CIP1}$ and p27 expression. In contrast, inhibition of miR-26a increased Id1 and decreased these cell cycle inhibitors in HUVECs (FIG. 2I). No regulation of Cyclin D2 or Cyclin E2 was observed with miR-26a overexpression or inhibition (FIG. 2N) Consistently, overexpression of miR-26a also decreased Id1 reporter gene activity by 2 fold in HUVECs (FIG. 2J). Taken together, these data suggest that in response to miR-26a, Smad1 and Id1 expression are reduced and cell cycle inhibitor genes increase, an effect that likely promotes endothelial cell growth arrest.

Example 5

MiR-26a Effects on Angiogenesis In-Vivo

Figure 3A:
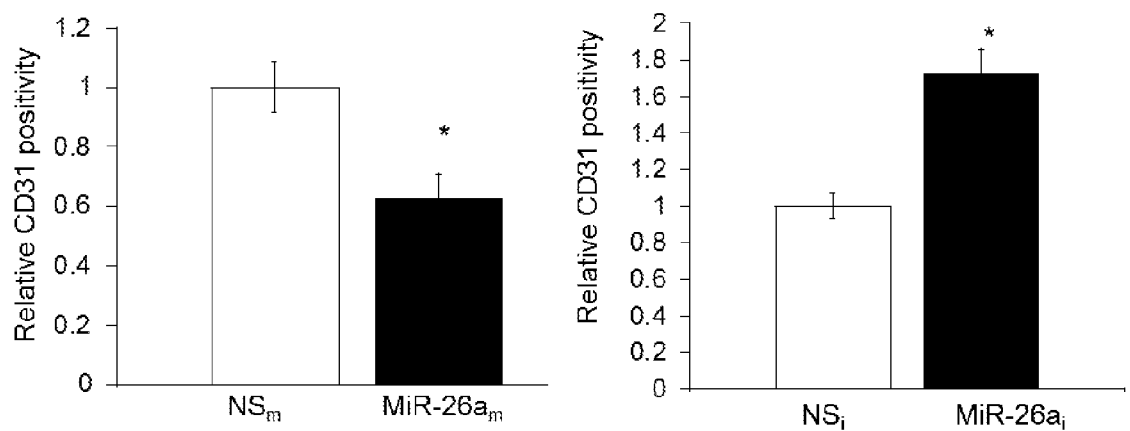
FIG. 3. MiR-26a regulates angiogenesis in-vivo. Inhibition of miR-26a enhances angiogenesis and decreases infarct size after acute myocardial infarction (MI) in mice. (A) Matrigel plugs (n=5) admixed with HUVECs transfected with miR-26a$_m$ to overexpress miR-26a or miR-26a$_i$ to inhibit miR26a expression in parallel with the scrambled control were implanted subcutaneously into nude mice and collected 7 days post implantation. Angiogenesis in matrigel plugs was analyzed using human CD31 Ab staining of the paraffin embedded matrigel sections (n=4-6 mice per group); *, p<0.05. (B) A single dose of 24 mg/kg was administered to mice (n=11-12) on day 0. Mice underwent acute myocardial infarction consisting of 45 minutes of left anterior descending artery (LAD) ligation on day 1 followed by the measurement of mir-26a expression in circulation on day 2. MiR-26a expression was increased in mice following myocardial injury compared to sham-injured control mice; *, p<0.05. (C) Hearts were harvested 3 days post injection and Western blotting was performed to detect SMAD1 protein expression. (D) TCD staining was performed on day 2 to quantify the infarct size. Data was normalized to the area at risk; *, p<0.05. Angiogenesis was further quantified by (E) CD31 or (F) isolectin staining of the heart sections collected on day 2; *, p<0.05. Number of CD31 or isolectin positive cells in the entire heart section was counted and normalized to the total area. Representative pictures of the CD31 and isolectin staining are shown. (G) Necrosis was quantified by Masson-Trichrome staining of the heart sections collected on day 2. Ischemic zone in the entire heart section was counted and normalized to the total area. Representative pictures of the staining are shown. Overexpression of miR-26a in-vivo decreases angiogenesis; *, p<0.05. (H) RNA from the quadricep muscle was harvested for quantitating the p21 and SMAD1 expression by RT-qPCR; *, p<0.05. (I) Representative pictures of SMAD1 and CD31 staining of the quadricep muscles collected on day 9. Co-localization (yellow) of CD31 and SMAD1 was quantified and normalized to the total area; *, p<0.05. (J) Representative pictures of Ki67 and DAPI staining of the quadricep muscles collected on day 9; *, p<0.01. (K-L) Number of CD31 positive cells were quantified in the quadricep muscle (K) and heart (L) and normalized to the total area; *, p<0.05. (M) Mice injected with the scrambled control were kept sedentary or exercised for 8 days. Quadriceps were harvested and stained for CD31; *, p<0.05. (N) Circulating miR-26a levels in healthy humans and patients with acute coronary syndrome was measure from the plasma collected from patients with acute coronary syndromes (n=14) including patient with unstable angina, non-ST elevation MI (NSTEMI), and STEMI compared to healthy subject controls with normal coronary angiograms (n=21). Circulating levels of miR-26a was analyzed by RT-qPCR; *, p<0.05. (O) Cardiac myocytes (CM) and non-myocytes (Non-CM) were harvested from the sham hearts (n=4-6) and miR-26a levels were detected by RT-qPCR; *, p<0.05. (P-Q) A single dose of 24 mg/kg was administered to mice (n=11-12) on day 0. Mice underwent acute myocardial infarction consisting of 45 minutes of left anterior descending artery (LAD) ligation on day 1 followed by the measurement of mir-26a expression in circulation on day 2; *, p<0.05. Reduced expression of miR-26a was verified by RT-qPCR analysis in heart (P) and peripheral blood plasma (Q). (R) Tunnel staining was performed on paraffin heart sections and Tunnel positive cells were counted and normalized to the total area. (S) Increased expression of miR-26a was verified by RT-qPCR analysis in the quadricep muscle on day 9; *, p<0.05.

To determine the role of miR-26a, matrigel plug implant studies were performed in vivo as described (Melero-Martin, J. M. and J. Bischoff, Methods Enzymol, 2008. 445: p. 303-29). Matrigel plugs (n=5) were implanted subcutaneously into nude mice with HUVECs overexpressing miR-26a or a scrambled control and matrigel plugs were left in mice over a one-week period. A marked reduction in angiogenesis was observed by CD31 staining of the matrigel (1.6 fold) in response to miR-26a overexpression compared to controls. Conversely, inhibition of miR-26a increased CD31 staining (by about 1.7 fold) suggesting increased angiogenesis (FIG. 3A).

Example 6

Figure 3B:
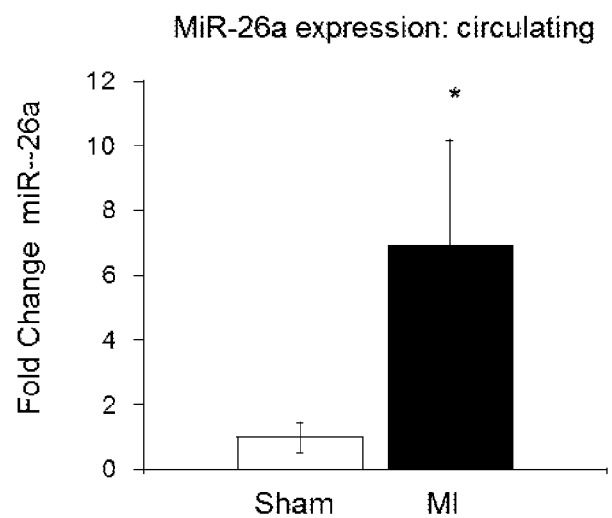
Figure 3C:
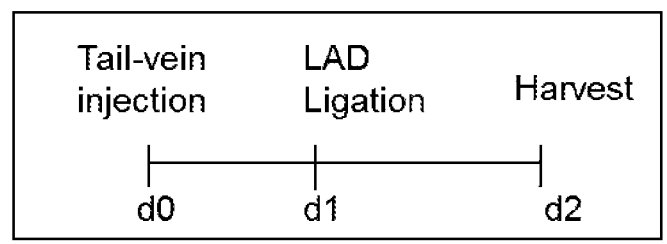
Figure 3C:
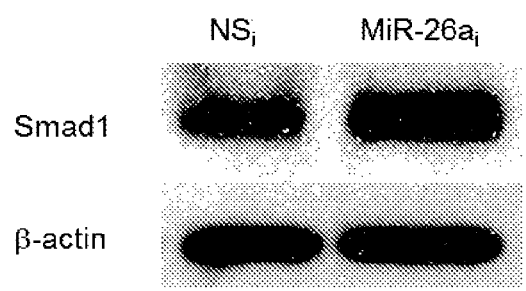
Figure 3D:
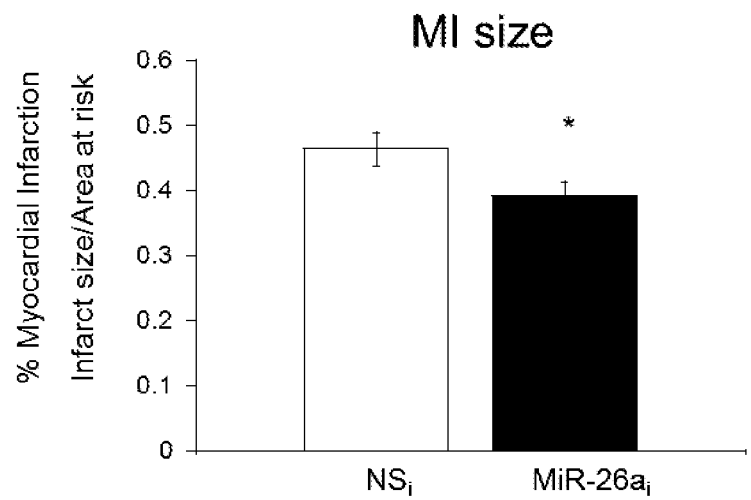
Figure 3E:
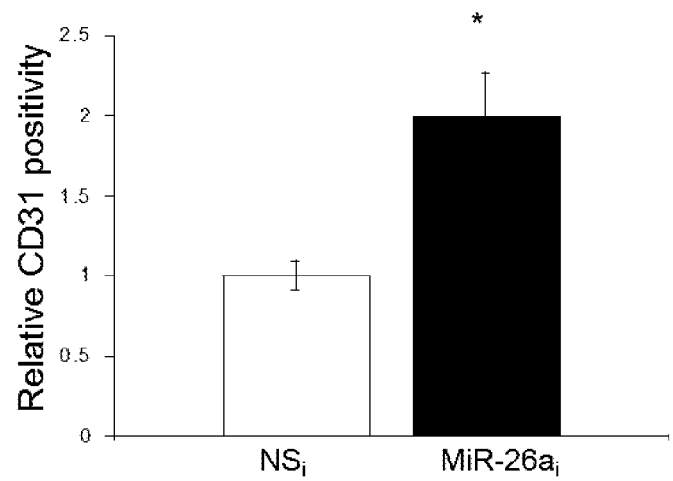
Figure 3F:
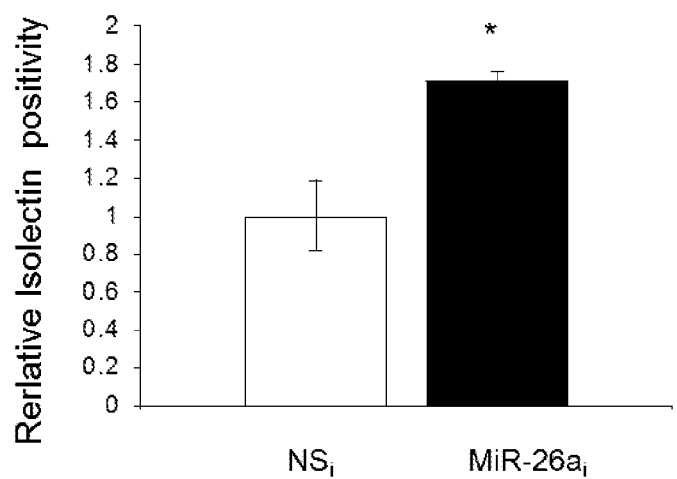
Figure 3G:
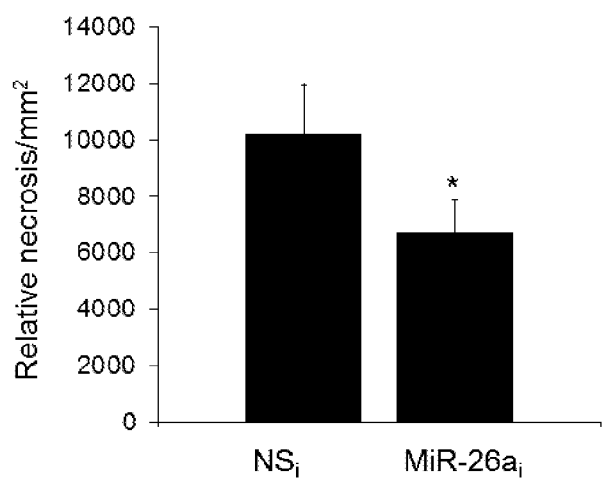
Figure 3H:
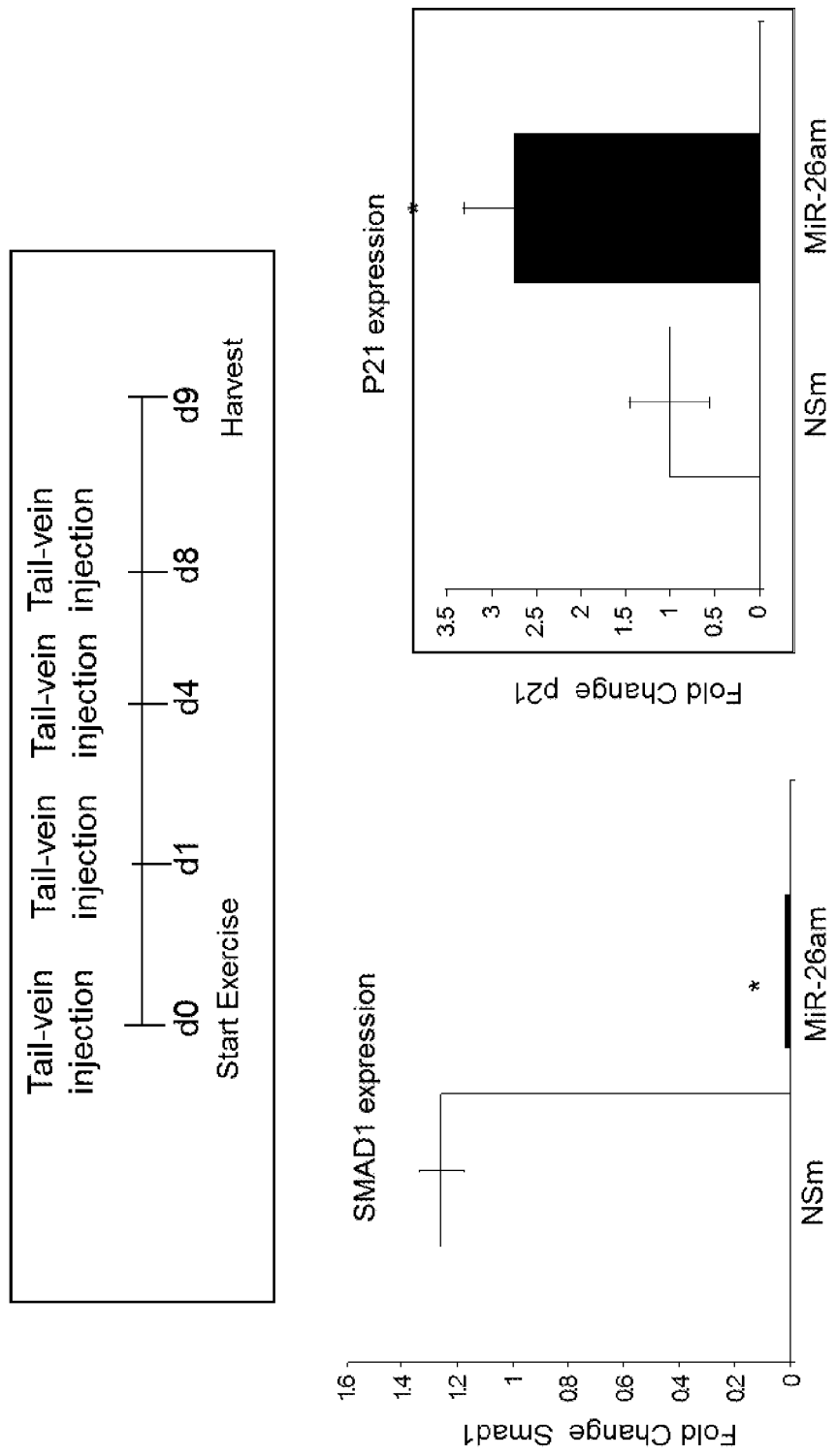
Figure 3I:
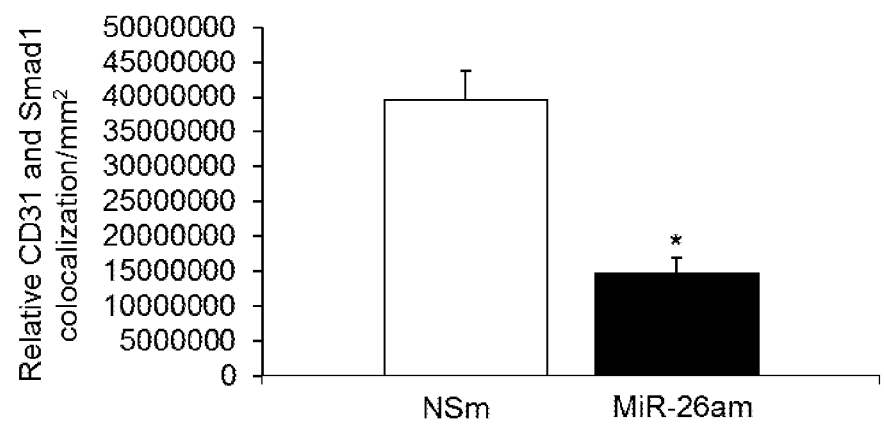
Figure 3J:
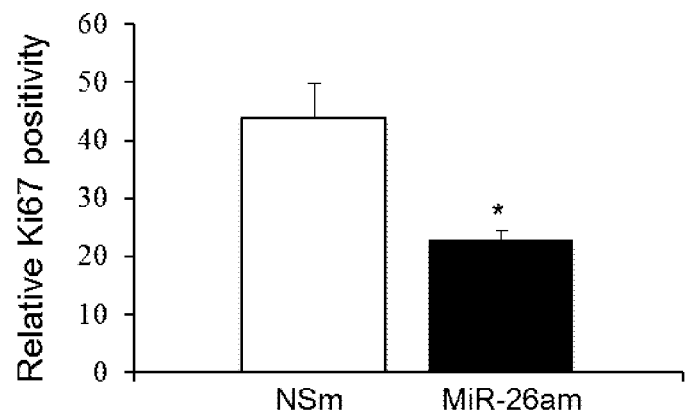
Figure 3K:
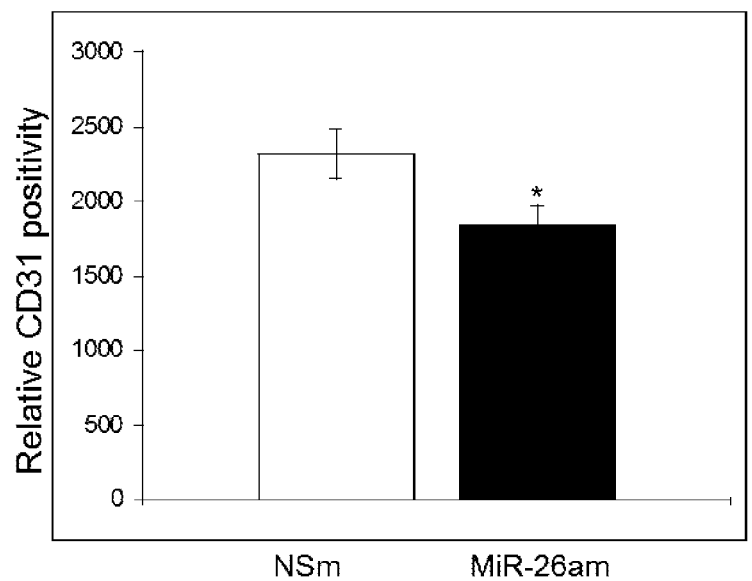
Figure 3L:
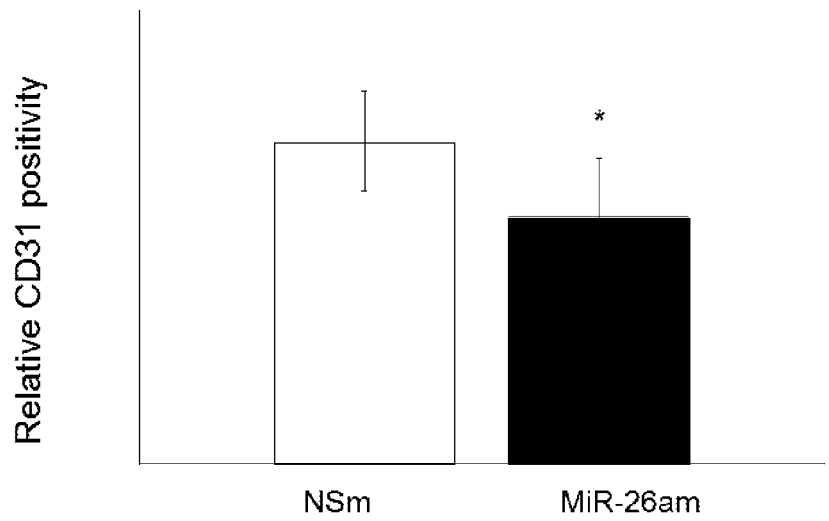
Figure 3M:
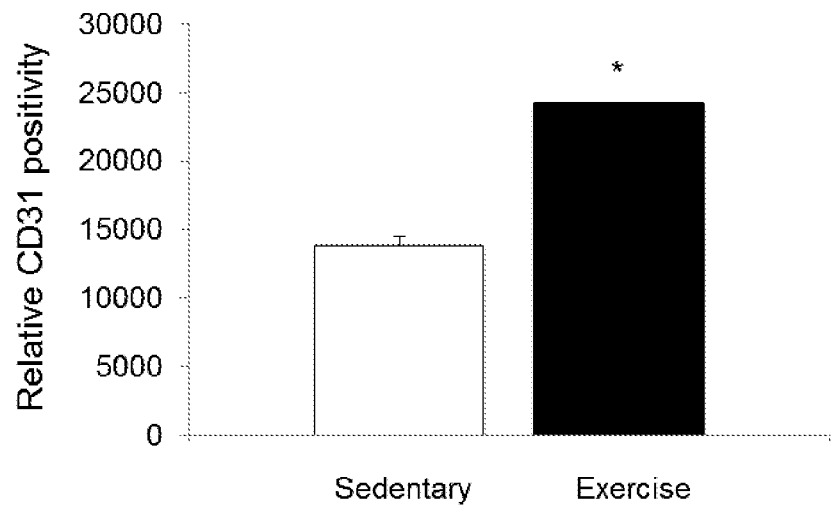
Figure 3N:
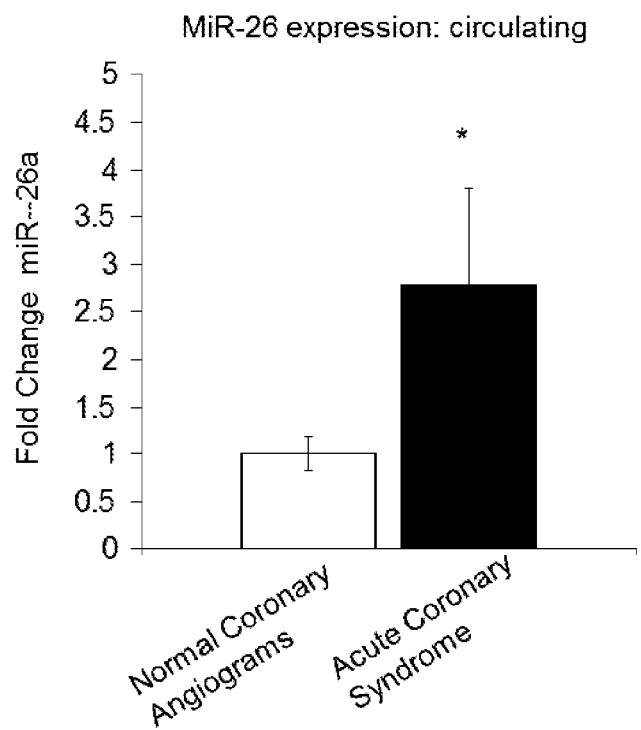
Figure 3O:
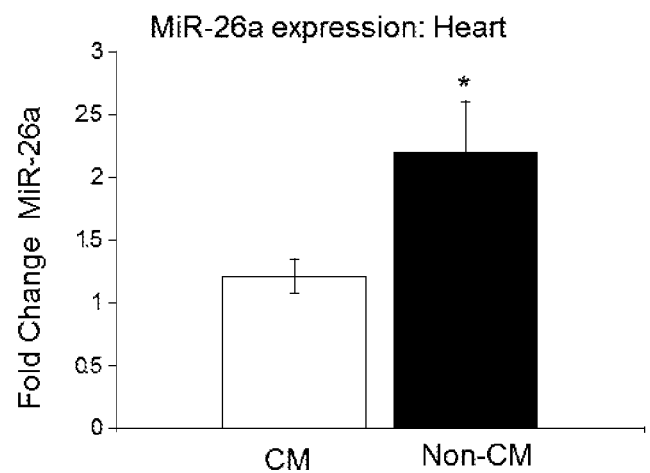
Figure 3P:
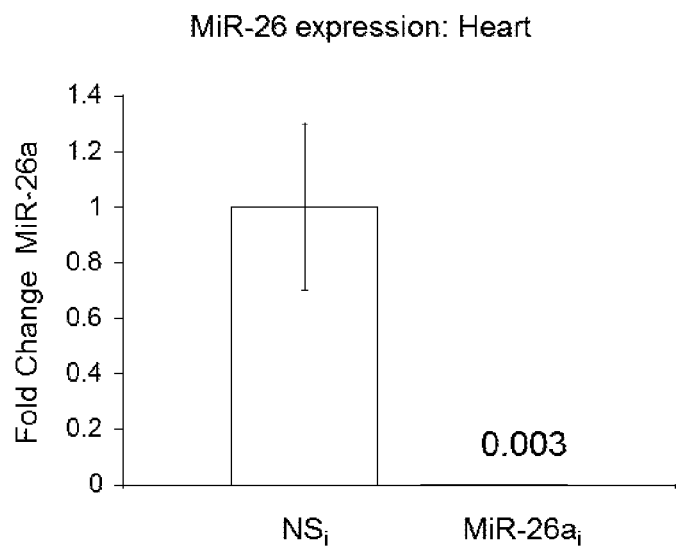
Figure 3Q:
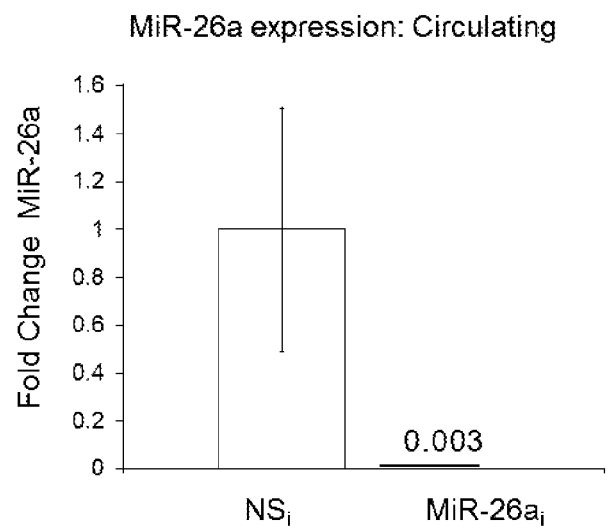
Figure 3R:
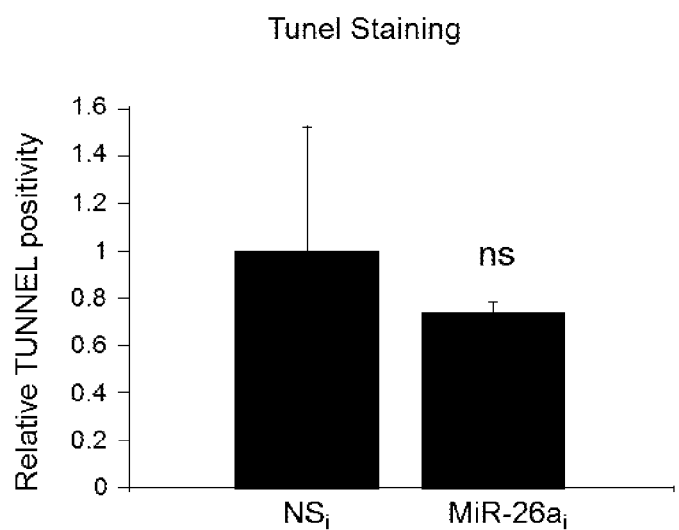
Figure 3S:
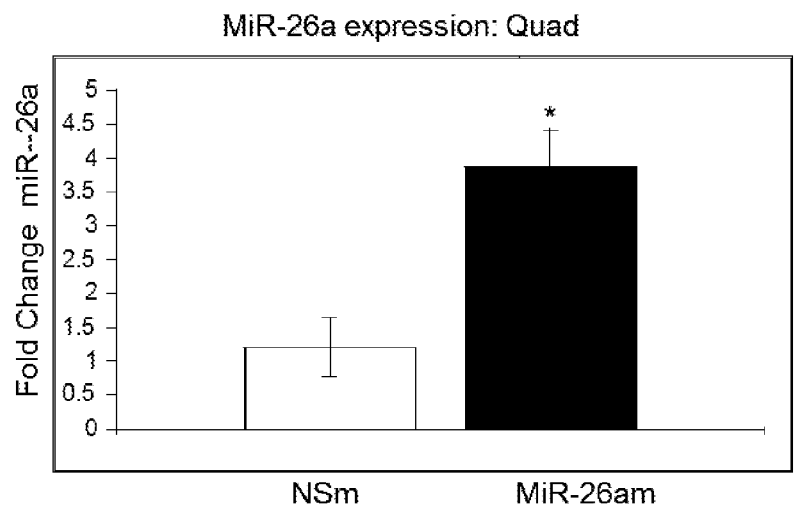

Inhibition of miR-26a Increases Angiogenesis and Reduces Infarct Size in a Model of Acute Myocardial Infarction (MI) In-Vivo To explore the effect of miR-26a on angiogenesis under pathophysiological conditions, a mouse model of acute myocardial infarction (MI) consisting of 45 minutes of left anterior descending artery (LAD) ligation was used. The expression levels of circulating miR-26a were examined; miR-26a expression was markedly increased in mice after MI compared to the sham control (FIG. 3B). In addition the expression of miR-26a in heart was expressed 50% higher in the non-myocyes fraction rich in smooth muscle cells as well as endothelial cells compared to the myocyte fraction (FIG. 3O). To explore the role of miR-26a in the context of acute MI, antagomiR-26a (n=12) or scrambled control antagomiRs (n=11) was systemically administered via tail-vein injections and 24 hrs later ischemia/reperfusion of the LAD (45 min.) in mice was performed. AntagomiR-26a effectively decreased both the circulating miR-26a levels and miR-26a expression in the heart (FIG. 3P) and increased SMAD1 expression (FIG. 3C). Mice that received miR-26a antagomiRs had significantly reduced myocardial infarct size compared to mice that received control antagomiRs (FIG. 3D). In addition, compared to controls, inhibition of miR-26a potently increased angiogenesis as measured by CD31 and isolectin staining in heart sections by 2-fold and 1.7-fold, respectively (FIG. 3E-F). Masson's trichrome stain may be used to differentiate necrotic myocardium (blue cytoplasm) from viable myocardium (red cytoplasm) often with purple myocardial cytoplasm surrounding a necrotic area (Ouyang, J., et al., Int J Clin Exp Pathol, 2009. 3(1): p. 98-105). Interestingly, miR-26a antagomiR injected mice showed less myocardial necrosis (by 1.5 fold) compared to mice that received control antagomiRs (FIG. 3G). Tunel staining showed no increase in apoptosis (FIG. 3R). Thus, targeting miR-26a induced angiogenesis and reduced infarct size after acute MI.

Example 7

Overexpression of miR-26a Decreases Exercise-Induced Angiogenesis

To explore whether miR-26a also regulated angiogenesis under physiological conditions, the effect of systemically delivered miR-26a mimics on exercise-induced angiogenesis in skeletal muscle was examined. After exercise for 8 days, overexpression of miR-26a decreased CD31 positivity both in quadriceps and in the hearts of these mice (FIG. 3K-L) whereas the mice injected with a scrambled control exhibited increased CD31 positivity with exercise (FIG. 3M). MiR-26a overexpression decreased SMAD1 and increased p21 expression (FIG. 3H) and decreased Ki67 positivity (FIG. 3J). Importantly, the reduced SMAD1 expression co-localized with CD31 positive cells (FIG. 3I). Collectively, these data indicate that increased miR-26a expression may adversely affect physiological angiogenesis such as in exercise.

Example 8

MiR-26a Expression Levels in Acute Coronary Syndromes

The development of angiogenesis is important in both acute and chronic coronary syndromes. To verify if levels of miR-26a in mice may also be regulated in an analogous manner in patients, circulating levels of miR-26a were examined in patients with acute coronary syndromes (n=14) including patient with non-ST elevation MI (NSTEMI) and STEMI compared to coronary angiograms with <20% lesions (n=21). As shown in FIG. 3N, circulating miR-26a levels were markedly increased (2.7 fold) compared to healthy controls patients in an analogous manner as observed after LAD-ligation in mice. These data suggest that miR-26a correlates with acute injury states such as myocardial infarction and indicate that targeting this miR facilitates the induction of angiogenesis.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of promoting angiogenesis for treating a disorder associated with impaired angiogenesis or blood flow to a tissue in the body in a subject, the method comprising administering to a subject in need thereof a therapeutically effective amount of an antagomir targeting microRNA-26a (miR-26a), wherein the antagomir is complementary to 7 or more nucleotides of mirR-26a and comprises the sequence ACTTGA (SEQ ID NO:5).

2. The method of claim 1, wherein the inhibitory nucleic acid comprises one or more locked nucleotides.

3. The method of claim 1, wherein the disorder is selected from the group consisting of ischemic heart disease, coronary artery disease, ischemic heart failure, peripheral artery disease (PAD), critical limb ischemia, and diabetic foot ulcers.

4. The method of claim 1, wherein the subject is a human.

5. The method of claim 1, wherein administering a therapeutically effective amount of an antagomir targeting microRNA-26a enhances angiogenesis in the subject.

6. The method of claim 5, wherein angiogenesis is enhanced in cardiac tissues.

7. The method of claim 6, wherein angiogenesis is enhanced in skeletal muscle.

8. The method of claim 1, wherein the antagomir targeting microRNA-26a is administered intravenously.

* * * * *

UNITED STATES PATENT AND TRADEMARK OFFICE
CERTIFICATE OF CORRECTION

| | | |
|---|---|---|
| PATENT NO. | : 9,322,015 B2 | Page 1 of 1 |
| APPLICATION NO. | : 14/003886 | |
| DATED | : April 26, 2016 | |
| INVENTOR(S) | : Mark W. Feinberg and Basak Icli | |

It is certified that error appears in the above-identified patent and that said Letters Patent is hereby corrected as shown below:

On title page, column 2 (Other Publications), line 33, delete "Chern.," and insert -- Chem., --;

On title page, column 2 (Other Publications), line 36, delete "Biol Chern," and insert -- Biol. Chem., --;

In the claims

In column 37, line 57 (approx.), Claim 1, delete "mirR-26a" and insert -- miR-26a --.

Signed and Sealed this
Twenty-eighth Day of June, 2016

Michelle K. Lee
*Director of the United States Patent and Trademark Office*

SEQUENCE LISTING

<160> NUMBER OF SEQ ID NOS: 12

<210> SEQ ID NO 1
<211> LENGTH: 77
<212> TYPE: RNA
<213> ORGANISM: Homo sapien

<400> SEQUENCE: 1
guggccucgu ucaaguaauc caggauaggc ugugcagguc ccaaugggcc uauucuuggu    60
uacuugcacg gggacgc                                                  77

<210> SEQ ID NO 2
<211> LENGTH: 84
<212> TYPE: RNA
<213> ORGANISM: Homo sapien

<400> SEQUENCE: 2
ggcuguggcu ggauucaagu aauccaggau aggcuguuuc caucugugag gccuauucuu    60
gauuacuugu uucggaggc agcu                                           84

<210> SEQ ID NO 3
<211> LENGTH: 22
<212> TYPE: RNA
<213> ORGANISM: Homo sapien

<400> SEQUENCE: 3
uucaaguaau ccaggauagg cu                                            22

<210> SEQ ID NO 4
<211> LENGTH: 6
<212> TYPE: RNA
<213> ORGANISM: Homo sapien

<400> SEQUENCE: 4 ucaagu                                                               6

<210> SEQ ID NO 5
<211> LENGTH: 6
<212> TYPE: DNA
<213> ORGANISM: Artificial Sequence
<220> FEATURE:
<223> OTHER INFORMATION: synthetically generated antagomir

<400> SEQUENCE: 5 acttga                                                               6

<210> SEQ ID NO 6
<211> LENGTH: 9
<212> TYPE: DNA
<213> ORGANISM: Artificial Sequence
<220> FEATURE:
<223> OTHER INFORMATION: synthetically generated antagomir

<400> SEQUENCE: 6 attacttga                                                            9

<210> SEQ ID NO 7
<211> LENGTH: 8
<212> TYPE: DNA
<213> ORGANISM: Artificial Sequence
<220> FEATURE:
<223> OTHER INFORMATION: synthetically generated antagomir

<400> SEQUENCE: 7

```
ttacttga                                                          8

<210> SEQ ID NO 8
<211> LENGTH: 7
<212> TYPE: DNA
<213> ORGANISM: Artificial Sequence
<220> FEATURE:
<223> OTHER INFORMATION: synthetically generated antagomir

<400> SEQUENCE: 8 tacttga                                                           7

<210> SEQ ID NO 9
<211> LENGTH: 22
<212> TYPE: RNA
<213> ORGANISM: Homo sapien

<400> SEQUENCE: 9
ccuauucuug guuacuugca cg                                         22

<210> SEQ ID NO 10
<211> LENGTH: 77
<212> TYPE: RNA
<213> ORGANISM: Homo sapien

<400> SEQUENCE: 10
ccgggaccca guucaaguaa uucaggauag guugugugcu guccagccug uucuccauua 60
cuuggcucgg ggaccgg                                               77

<210> SEQ ID NO 11
<211> LENGTH: 21
<212> TYPE: RNA
<213> ORGANISM: Homo sapien

<400> SEQUENCE: 11
uucaaguaau ucaggauagg u                                          21

<210> SEQ ID NO 12
<211> LENGTH: 22
<212> TYPE: RNA
<213> ORGANISM: Homo sapien

<400> SEQUENCE: 12
ccuguucucc auuacuuggc uc                                         22
```